United States Patent
Bartek et al.

(10) Patent No.: US 10,457,874 B2
(45) Date of Patent: Oct. 29, 2019

(54) DEPOLYMERIZATION PROCESS

(71) Applicant: CIRIS ENERGY, INC., Centennial, CO (US)

(72) Inventors: Robert Bartek, Centennial, CO (US); Bahman Rejai, Denver, CO (US)

(73) Assignee: CIRIS ENERGY, INC, Centennial, CO (US)

( * ) Notice: Subject to any disclaimer, the term of this patent is extended or adjusted under 35 U.S.C. 154(b) by 22 days.

(21) Appl. No.: 15/547,999

(22) PCT Filed: Feb. 9, 2016

(86) PCT No.: PCT/US2016/017059
§ 371 (c)(1),
(2) Date: Aug. 1, 2017

(87) PCT Pub. No.: WO2016/130494
PCT Pub. Date: Aug. 18, 2016

(65) Prior Publication Data
US 2018/0023007 A1    Jan. 25, 2018

Related U.S. Application Data

(60) Provisional application No. 62/114,299, filed on Feb. 10, 2015.

(51) Int. Cl.
| | |
|---|---|
| *C10G 1/08* | (2006.01) |
| *C10G 27/10* | (2006.01) |
| *C10G 32/00* | (2006.01) |
| *C12P 3/00* | (2006.01) |
| *C12P 5/02* | (2006.01) |
| *C12N 1/00* | (2006.01) |

(52) U.S. Cl.
CPC ............. *C10G 1/086* (2013.01); *C10G 27/10* (2013.01); *C10G 32/00* (2013.01); *C12N 1/00* (2013.01); *C12P 3/00* (2013.01); *C12P 5/023* (2013.01)

(58) Field of Classification Search
CPC .................. C07C 29/156; C07C 31/08; C01B 2203/0233; C01B 2203/025; C01B 2203/0283; C01B 32/05; C01B 32/40; C01B 32/50; C01B 2203/02; C01B 2203/0255; C01B 2203/1241; C01B 3/344; C01B 2202/06; C01B 2202/08; C01B 2203/0238; C01B 2203/0415; C01B 2203/0811; C01B 2203/0822; C01B 2203/0827; C01B 32/162; C01B 3/42; C01B 3/44; C01B 832/162; Y02P 20/134; Y02P 20/133; Y02P 20/128; Y02P 20/142; B01J 23/85; B01J 23/882; B01J 27/049; B01J 27/0515; B01J 37/03; B01J 37/20; B01J 8/12; B01J 19/00; B01J 23/8878; B01J 35/10; B01J 37/0225; B01J 37/0226; G01N 31/10; C10J 2300/1807; C10J 2300/0916; C10J 2300/093; C10J 2300/0953; C10J 3/57; C10J 2300/0993; C10J 2300/1637; C10J 3/463; H01M 2008/1293; H01M 2008/147; H01M 2250/00; H01M 8/0656; H01M 8/18; Y02E 20/18; Y02E 60/526; Y02E 60/528; Y02E 60/324; C10G 1/086; C10G 27/10; C10G 32/00; C12P 3/00; C12P 5/023; B82Y 30/00; B82Y 40/00; C10K 1/06; C10K 1/101; C10K 3/001; C10K 3/006; C25B 1/24; C25B 3/06; C25B 9/10; C25B 9/18; Y10S 977/752; Y10S 977/843

See application file for complete search history.

(56) References Cited

U.S. PATENT DOCUMENTS

| | | | |
|---|---|---|---|
| 2,193,337 | A | 3/1940 | Leicester |
| 2,461,740 | A | 2/1949 | Kiebler |
| 2,702,240 | A | 2/1955 | Rees et al. |
| 3,977,844 | A | 8/1976 | Van Slyke |
| 3,996,161 | A | 12/1976 | Chia |
| 4,322,243 | A | 3/1982 | Frewer et al. |
| 4,345,098 | A | 8/1982 | Schep |
| 4,617,027 | A | 10/1986 | Lang |
| 5,714,091 | A | 2/1998 | Mazanec et al. |
| 6,663,681 | B2 | 12/2003 | Kindig et al. |

(Continued)

FOREIGN PATENT DOCUMENTS

| | | |
|---|---|---|
| CN | CN102985514 A | 3/2013 |
| CN | CN104073278 A | 10/2014 |

(Continued)

OTHER PUBLICATIONS

EA Office Action; dated Apr. 5, 2018 for EA Application No. 201791539/28.

(Continued)

*Primary Examiner* — Deborah K Ware
(74) *Attorney, Agent, or Firm* — Mendelsohn Dunleavy, PC

(57) ABSTRACT

A method for solubilizing a carbonaceous feedstock. The method includes steps of reacting a mixture of the carbonaceous feedstock with a metal oxide including a metal at a first, higher oxidation state to reduce the metal of the metal oxide to a second, lower oxidation state by releasing at least one oxygen atom from the metal oxide. The released oxygen from the metal oxide is used to oxidize the carbonaceous feedstock. At least a portion of the metal or metal oxide containing the metal at the second, lower oxidation state is then oxidized to the metal oxide containing the metal at the first, higher oxidation state for reuse in the reaction step.

18 Claims, 4 Drawing Sheets

(56) References Cited

U.S. PATENT DOCUMENTS

| | | |
|---|---|---|
| 6,669,917 B2 | 12/2003 | Lyon |
| 7,922,782 B2 | 4/2011 | Sheth |
| 8,088,614 B2 | 2/2012 | Vick et al. |
| 8,435,920 B2 | 5/2013 | White et al. |
| 8,491,782 B2 | 7/2013 | Reynolds et al. |
| 8,679,322 B2 | 3/2014 | Marzin et al. |
| 2003/0232892 A1 | 12/2003 | Guerra-Santos et al. |
| 2006/0199987 A1 | 9/2006 | Kuechler et al. |
| 2006/0210622 A1 | 9/2006 | Pace et al. |
| 2007/0269526 A1 | 11/2007 | Bos et al. |
| 2009/0216056 A1 | 8/2009 | Beeckman et al. |
| 2010/0139913 A1 | 6/2010 | Downey |
| 2010/0262987 A1 | 10/2010 | Imanilov |
| 2011/0045086 A1 | 2/2011 | McAffer et al. |
| 2011/0262987 A1 | 10/2011 | Downey |
| 2012/0064609 A1 | 3/2012 | Clement et al. |
| 2012/0160658 A1 | 6/2012 | Bartek et al. |
| 2012/0199054 A1 | 8/2012 | Alban et al. |
| 2012/0238646 A1 | 9/2012 | Bi et al. |
| 2012/0319051 A1 | 12/2012 | Rifflart et al. |
| 2013/0032761 A1 | 2/2013 | Fan et al. |
| 2013/0079566 A1 | 3/2013 | Lin |

FOREIGN PATENT DOCUMENTS

| | | |
|---|---|---|
| EP | 0220933 A1 | 5/1987 |
| EP | 1116694 B1 | 7/2001 |
| EP | 2231118 B1 | 9/2010 |
| WO | WO2007006398 A1 | 1/2007 |
| WO | WO2008088452 A2 | 7/2008 |
| WO | WO2013057518 A1 | 4/2013 |
| WO | WO2014185957 A1 | 11/2014 |

OTHER PUBLICATIONS

SG Written Opinion; dated Apr. 27, 2018 for SG Application No. 11201706343V.

European Search Report; dated Jun. 19, 2018 for EP Application No. 16749677.7.

Request for Corrected SG Written Opinion; dated Jun. 8, 2018 for EP Application No. 16749677.7.

International Search Report and Written Opinion; dated Jul. 1, 2016 for PCT Application No. PCT/US2016/017059.

Talmor, E. "Two-phase downflow through catalyst beds: Part I. Flow maps." AIChE Journal 23.6 (1977): 868-874.

Collinson, S. R., and Wim Thielemans. "The catalytic oxidation of biomass to new materials focusing on starch, cellulose and lignin." Coordination chemistry reviews 254.15 (2010): 1854-1870.

Zakzeski, Joseph, Anna L. Jongerius, and Bert M. Weckhuysen. "Transition metal catalyzed oxidation of Alcell lignin, soda lignin, and lignin model compounds in ionic liquids." Green chemistry 12.7 (2010): 1225-1236.

Kobayashi, Hirokazu, Hidetoshi Ohta, and Atsushi Fukuoka. "Conversion of lignocellulose into renewable chemicals by heterogeneous catalysis." Catalysis Science & Technology 2.5 (2012): 869-883.

Blume, A., "Bitumen Blowing Unit Converts Residues to Asphatl," Hydrocarbon Processing, 2014, pp. 1-4.

Xu, Chunping, et al. "Lignin depolymerisation strategies: towards valuable chemicals and fuels." Chemical Society Reviews 43.22 (2014): 7485-7500.

Demirbas, Ayhan, Temel Ozturk, and M. Fatih Demirbas. "Recovery of energy and chemicals from carbonaceous materials." Energy Sources, Part A 28.16 (2006): 1473-1482.

First Office Action from the State Intellectual Property Office of China; Patent Application No. 201680009811.5; dated Dec. 3, 2018.

Tosoni, S. et al., "$TiO_2$ and $ZrO_2$ in biomass conversion: why catalyst reduction helps.", Philosophical Transactions of the Royal Society A; vol. 376 Issue 2110 (2017) pp. 20170056.

DEPOLYMERIZATION PROCESS

FIELD OF THE INVENTION

The present invention relates to conversion of insoluble carbonaceous feedstocks to water soluble products. In particular, the present invention is directed to oxidation of carbonaceous feedstocks using a metal oxide as an oxygen carrier to produce soluble chemical products and/or biodegradable substrates.

DESCRIPTION OF THE RELATED TECHNOLOGY

Carbonaceous feedstocks, especially those that have previously been considered less suitable for use as fuel, have received renewed attention. These carbonaceous feedstocks may be converted to products ranging from clean fuels to raw materials for various industries, such as natural gas, hydrogen, alcohols, organic acids, and short-chain hydrocarbons. For example, carbonaceous feedstocks can be gasified at elevated temperature and pressure to produce a synthetic gas stream that can subsequently be converted to gaseous fuel.

Conversion of coal or lignocellulosic materials to valuable fuels and raw chemicals has been studied and described extensively. Generally, in such conversion processes, coal or lignocellulosic materials is depolymerized in varying degrees to its organic constituents. These conversion technologies fall under three main categories: hydroliquefaction or direct liquefaction, pyrolysis and gasification. The goal in all these technologies is coal or lignocellulosic materials beneficiation by making a mixture of higher value fuels, raw chemicals or a precursor to desirable fuels or raw chemicals. However, these processes typically take place either at high temperature and/or high pressure and/or they use expensive hydrogen and organic solvents.

For example, the indirect coal or lignocellulosic materials liquefaction process consists of a gasification step at temperatures greater than about 700° C. in the presence of oxygen or air to make syngas (a mix of CO & $H_2$), followed by at least one catalytic step which converts the syngas to liquid hydrocarbons. The coal or lignocellulosic materials gasification step requires feeding the coal or lignocellulosic materials into a heated chamber (the "gasifier") along with a controlled and/or limited amount of oxygen and optionally steam. In contrast to incineration or combustion, which operates with excess oxygen to produce $CO_2$, $H_2O$, $SO_x$ (including products such as SO, $SO_2$, $SO_3$, $S_7O_2$, $S_6O_2$, $S_2O_2$, etc), and $NO_x$ (including such products as NO, $NO_2$, $N_2O$), coal or lignocellulosic materials gasification produces a raw gas composition comprising CO, $H_2$, $H_2S$, and $NH_3$. After clean-up, the primary gasification products of interest are $H_2$ and CO. See Demirbas, "Recovery of Energy and Chemicals from Carbonaceous Materials," *Energy Sources*, Part A, vol. 28, pages 1473-1482, 2006. This process is very capital intensive.

Direct coal or lignocellulosic materials liquefaction processes convert coal or lignocellulosic materials into liquid products directly, without the intermediate step of gasification, by breaking down the high molecular weight organic molecules in coal or lignocellulosic materials with solvents and catalysts in a high pressure and high temperature environment in the presence of hydrogen. Since the liquid products such as liquid hydrocarbons generally have a higher hydrogen-carbon molar ratio than coal or lignocellulosic materials, either hydrogenation or oxygen and carbon-rejection processes are employed in the direct coal or lignocellulosic materials liquefaction process. This process requires significant energy consumption and, at industrial scales (thousands of barrels/day), large capital investments.

Other carbonaceous feedstocks may also be solubilized to produce valuable starting materials for various industrial applications. U.S. Pat. No. 4,345,098 discloses a process for producing an isomerized benzene carboxylic acid salt by treating a mixture of a carbonaceous feedstock, water, and a water soluble reagent comprising a Group Ia or IIa metal with oxygen under conditions sufficient to convert at least a portion of the aromatic compounds in the carbonaceous material to a benzene carboxylic acid salt of the metal, and isomerizing the benzene carboxylic acid salt by heating. The isomerized benzene carboxylic acid salt is then recovered from the reaction mixture. The process uses a preferred temperature in the range of from 200° C. to 350° C. and a pressure of 1700 psig.

US 2012/0064609 discloses a method for solubilizing coal or lignocellulosic materials by treating the coal or lignocellulosic materials with a composition comprising a pyrophosphate or a derivative thereof. Solubilization of the coal or lignocellulosic materials can be carried out in a subterranean formation, in a terrestrial formation or in an ex situ reactor. The solubilization process requires a temperature ranging from ambient temperature to up to 500° C. and a pressure in a range of from atmospheric pressure to about 100 psi.

U.S. Pat. No. 2,193,337 discloses a process for producing oxalic acid salts by heating a carbonaceous feedstock such as sawdust, woodchips, peat or coal, with oxygen-containing gases at elevated pressures and temperatures in the presence of at least 10 times the weight of the carbonaceous feedstock of water and preferably an oxide or hydroxide of an alkali or alkaline earth metal, in an amount of 1.5 to 4 times the weight of the feedstock. The produced oxalic acid, as well as other organic acids such as mellitic acid, benzoic acid, or acetic acid, may then be isolated from the resulting reaction products. The examples in the patent show that solubilization is operated at a preferred temperature of 180° C. and a preferred pressure of 20 atmospheres for a duration of about 2 hours.

U.S. Pat. No. 8,435,920 discloses a process for gasification of a fuel such as diesel, gasoline, jet fuel, alcohols, glycerol, and plant oils. The process comprises contacting the fuel with an oxygen-carrying catalyst at a temperature up to 900° C., and then with an oxidizing gas to produce $H_2$, CO, $CO_2$, or $CH_4$. The catalyst is alternately reduced and then regenerated to an oxygenated state in the process. The catalyst comprises at least one metal oxide-containing composition of the following formulae: (a) $Ce_xB_yB'_zB''O_\delta$, wherein B=Ba, Sr, Ca, or Zr; B'=Mn, Co, and/or Fe; B''=Cu; $0.01<x<0.99$; $0<y<0.6$; $0<z<0.5$; (b) $Ce_{1-x-y}Ni_xB_yO_{2-*}$, wherein B=Zr, Ba, Ca, La, or K; $0.02<x<0.1$; $0<y<0.1$; and $0.02<*<0.15$; and $1<\delta<2.2$ and (c) coal ash either as a catalyst material itself or as a support for the metal oxides.

US 2012/0199054 discloses a process for production of energy from a fuel, comprising oxidizing the fuel by contacting the fuel with at least one oxygen-charged solid compound with concomitant reduction of the solid compound, recovering the reduced solid compound, exothermically reoxidizing at least a fraction of the recovered solid compound by contacting the recovered solid compound with an oxygen-comprising gas, and recovering the reoxidized solid compound to be reused. The oxygen-comprising gas may be air or a gas comprising a concentration by volume of oxygen of between 22% and 100%.

US 2012/0319051 discloses a cyclic process for producing a synthesis gas from hydrocarbons, comprising successive steps of oxidizing an oxidizable solid that is an oxygen carrier and a thermal vector, purging air from the oxidized solid, combusting the oxidized solid with the hydrocarbon to produce $CO_2$, and producing synthesis gas by mixing $CO_2$, steam and methane. The oxidizable solid is an oxygen-carrying solid containing a metal selected from Ni, W, Mn, Rh, Co, Sr, Ba, Pt, Fe, Cu, Mo, Pd, Ag, and mixtures thereof. The temperature used in this process is typically between 700° C. and 1000° C., and the pressure is in the range of 20 to 100 bar.

U.S. Pat. No. 7,922,782 discloses a gasification process for converting carbonaceous materials to methane and an apparatus for performing the gasification process. The gasification process includes reacting steam and a carbonaceous material in the presence of an alkali metal catalyst in a gasification reactor to produce combustible gases and char particles, treating a stream of such char particles in an alkali metal catalyst recovery system to recover the catalyst constituents as alkali metal compounds, and recycling the recovered alkali metal catalyst. The alkali metal catalyst may be an inorganic alkali metal salt, an organic alkali metal salt, an alkali metal hydroxide, an alkali metal oxide, an alkali metal carbonate, an alkali metal bicarbonate, or a pure metal, or a combination of two or more of these compounds/metals.

One major drawback of the processes disclosed in the prior art as described in the above patents is the use of relatively high temperature, pressure, and/or expensive solvents such as alkali metal hydroxides or oxidizing agents such as pure $O_2$ or other costly oxidizers. Such severe conditions result in prohibitive raw material and/or energy costs, making such processes uneconomical on an industrial scale. These processes also typically result in a product stream or gaseous products that are incompatible with a subsequent microbial conversion step.

An improved process is needed that utilizes milder conditions and yet provides efficient oxidative depolymerization of carbonaceous feedstocks and enhances the biodegradability of the resultant products to chemicals and biogas. Such an improved process can lower the cost of producing clean fuels and industrial raw materials from carbonaceous feedstocks thereby improving the economic viability of such processes.

SUMMARY OF THE INVENTION

[1]. The present invention provides a method for solubilizing a carbonaceous feedstock, comprising the steps of a. reacting a mixture of the carbonaceous feedstock with a metal oxide including a metal at a first, higher oxidation state to reduce the metal of the metal oxide to a second, lower oxidation state by releasing at least one oxygen atom to oxidize at least one component of the carbonaceous feedstock; b. oxidizing at least a portion of the metal or metal oxide containing the metal at the second, lower oxidation state to the first, higher oxidation state, and c. recycling at least a portion of the metal oxide containing the metal at the first, higher oxidation state from step (b) back to step (a).

[2]. The method of [1], wherein the metal oxide comprises a transition metal selected from the group consisting of lanthanides and actinides.

[3]. The method of any one of [1-2], where the metal oxide comprises a metal selected from Fe, Ti, Cu, Ni, V, Cr, Mn, Co, Mo, La, Ce, Zr, Sr, W, Rh, Ba, Pt, Pd, and Ag.

[4]. The method of any one of [1-3], wherein in the reacting step the weight ratio of metal oxide to the carbonaceous feedstock is in a range of from about 0.1:100 to about 10:100, or from about 0.5:100 to about 5:100, or from about 1:100 to about 3:100.

[5]. The method of any one of [1-4], wherein the metal oxide is on an inert support.

[6]. The method of [5], wherein the inert support comprises a material selected from carbon, activated carbon, pumice, alumina, silica, silica-alumina, magnesia, diatomaceous earth, bauxite, titania, zirconia, clay, magnesium silicate, silicon carbide, zeolites, ceramics, carborundum, quartz, thoria, chromite, rutile, illmenite zircon, bauxite and combinations thereof.

[7]. The method of any one of [5-6], further comprising the step of heating the inert support prior to step (a) to enable transfer of heat from the insert support to the mixture in step (a).

[8]. The method of any one of [5-7], wherein the inert support is in a form selected from particles, extrudates, monoliths, fibers, mesh, and a net.

[9]. The method of any one of [1-8], wherein step (a) is conducted in the presence of at least one oxidizing agent.

[10]. The method of [9], wherein the at least one oxidizing agent is selected from the group consisting of air, oxygen-enriched air, oxygen, ozone, perchlorates, carbon dioxide, nitrous oxide, oxides, superoxides, permanganates, chlorates, peroxides, hypochlorites and nitrates.

[11]. The method of any one of [9-10], wherein the at least one oxidizing agent comprises a cation selected from metal, hydrogen and ammonium ions.

[12]. The method of any one of [1-11], wherein step (a) is performed at a temperature in a range of from about 140° C. to about 270° C., or from about 200° C. to about 220° C.

[13]. The method of any one of [1-12], wherein step (a) is performed at a pressure in a range of from about 200 psia to about 1000 psia, or from about 700 psia to about 900 psia.

[14]. The method of any one of [1-13], wherein the mixture reacted in step (a) comprises at least one solubilizing agent selected from the group consisting of mineral acids and mineral bases.

[15]. The method of any one of [1-14], wherein step (a) is configured as multiple sequential steps.

[16]. The method of [15], wherein each of the multiple sequential steps is carried out with at least one difference in a reaction condition of temperature, pressure and duration, or a composition of an oxidizing agent.

[17]. The method of any one of [1-16], wherein step (a) is performed for a duration of from about 1 minute to about 5 hours, or from about 1 minutes to about 2 hours, or from about 1 minute to about 1 hour, or from about 5 minutes to about 30 minutes.

[18]. The method of any one of [1-17], further comprising the step of digesting the solubilized carbonaceous feedstock from step (a) with at least one microorganism.

[19]. The method of [18], wherein the digesting step is a process selected from an aerobic process, an anaerobic process and a combination of an aerobic process and an anaerobic process.

[20]. The method of any one of [1-19], wherein the carbonaceous feedstock is selected from the group consisting of coal, lignite, tar sands, tars, crude oils, peat, pitch, resins, lignin, latex rubber, waxes, agricultural wastes, bark, wood, and algae cake.

[21]. The method of any one of [1-20], wherein step (a) is performed in a reaction vessel selected from a bubble column reactor and a trickle bed reactor.

DETAILED DESCRIPTION OF THE PREFERRED EMBODIMENT(S)

Figure 1:
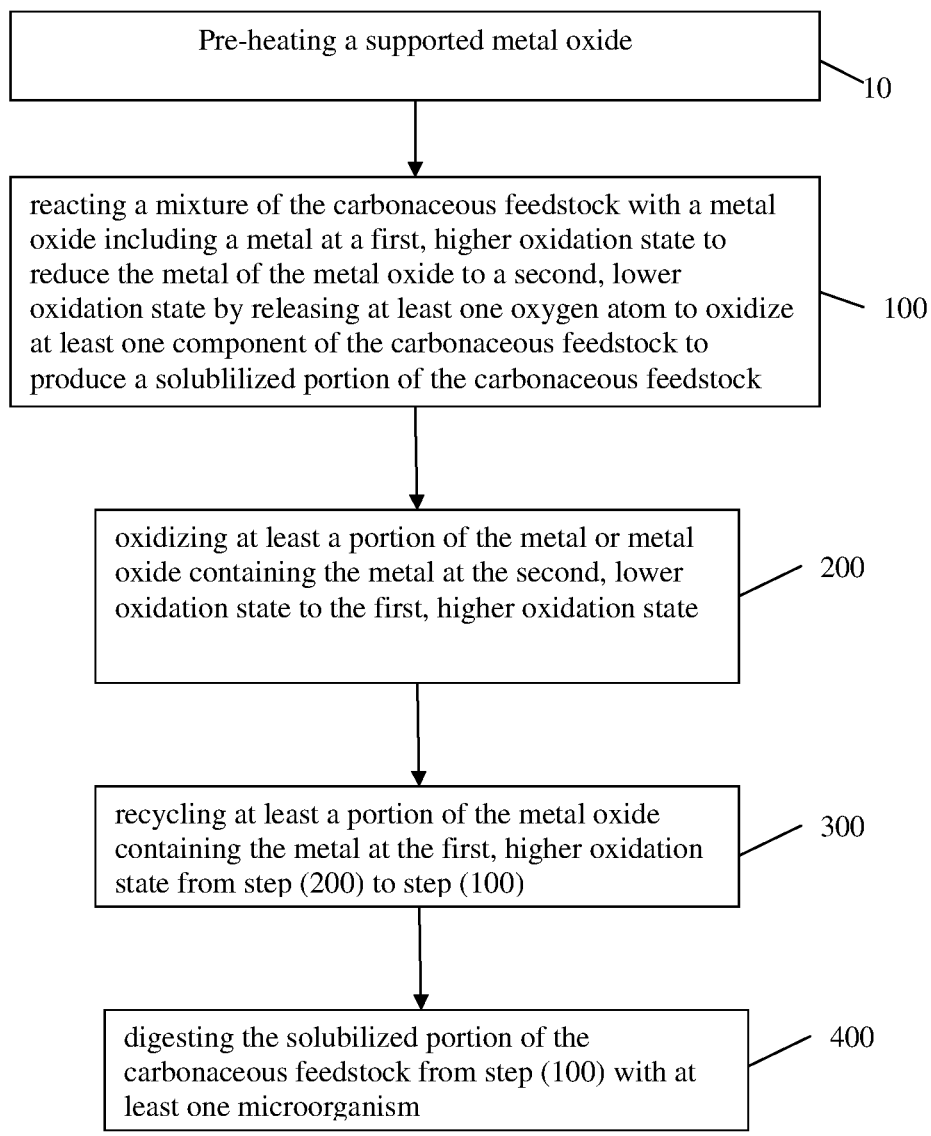
FIG. 1 is a flow chart that shows a method according to one embodiment of the present invention.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, any value within a disclosed range whether explicitly mentioned or not, as well as specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

As used herein, the term "bioconversion" refers to conversion of solubilized carbonaceous feedstocks by a microorganism into a product that may include methane and other useful gases and liquid components. The products of bioconversion include organic materials such as hydrocarbons, for example, methane, ethane, propane, butane, and other small organic compounds, as well as fatty acids, dicarboxylic acids, ketones, aldehydes, and alcohols that are useful as fuels or raw materials for chemical processes or other industrial applications, and other materials, such as gases, including hydrogen and carbon dioxide.

As used herein, the term "carbonaceous feedstock" includes naturally occurring polymeric substances, such as coal, lignite, tar sands, tars, crude oils, peat, leonardite, pitch, resins, lignin, latex rubber, waxes, agricultural wastes, bark, wood, any type of renewable biomass and other products from trees, algae cake, and other recalcitrant organic matter, and may also include lower-valued by-products from petroleum refining and chemical manufacturing, such as crude oil atmospheric bottoms, crude oil vacuum residues, residua from fluid catalytic cracking, petroleum coke, coker and other thermal cracking gas oils and bottoms, raffinates, asphalts, polynuclear aromatics, and the like, and may even include synthetic polymer wastes such as polyethylene, polypropylene, polystyrene, polyesters, polyacrylics, and the like.

In one embodiment of the present invention, the carbonaceous feedstock comprises coal, lignite, tar sands, tars, crude oils, peat, pitch, resins, lignin, latex rubber, waxes, petroleum coke, agricultural wastes, bark, wood, and algae concentrate.

Algae concentrate, such as algae paste or algae cake, is a residue to obtained by separating algae from the medium in which they grow, which is typically water based. The concentrated algae may be able to be processed in a form containing small amount of residual water. The algae may be separated from the medium in a variety of ways, for example, by filtration.

As used herein, the term "coal" refers to any of the series of carbonaceous fuels ranging from lignite to anthracite. The members of the series differ from each other in the relative amounts of moisture, volatile matter, and fixed carbon they contain. Coal is comprised mostly of carbon, hydrogen, sulfur, oxygen, nitrogen, ash and entrained water, predominantly in the form of large molecules having numerous carbon double bonds. Low rank coal deposits are mostly comprised of coal and water. Coal is formed from plants that have been fossilized through successive deoxidation and condensation processes.

As used herein, the term "microorganism" includes bacteria, archaea and fungi. The microorganisms, by example, may include: *Thermotogales, Cytophaga* group, *Azospirillum* group, *Paracoccus* subgroup, *Sphingomonas* group, *Nitrosomonas* group, *Azoarcus* group, *Acidovorax* subgroup, *Oxalobacter* group, *Thiobacillus* group, *Xanthomonas* group, *Oceanospirillum* group, *Pseudomonas* and relatives, *Marinobacter hydrocarbonoclaticus* group, *Pseudoalteromonas* group, *Vibrio* subgroup, *Aeromonas* group, *Desulfovibrio* group, *Desulfuromonas* group, *Desulfobulbus* assemblage, *Campylobacter* group, *Acidimicrobium* group, *Frankia* subgroup, *Arthrobacter* and relatives, *Nocardiodes* subgroup, *Thermoanaerobacter* and relatives, *Bacillus megaterium* group, *Carnobacterium* group, *Clostridium* and relatives, and archaea such as *Archaeoglobales, Methanobacteriales, Methanomicrobacteria* and relatives, *Methanopyrales,* and *Methanococcales.*

More specific examples of microorganisms may include, for example, *Aerobacter, Aeromonas, Alcaligenes, Bacillus, Bacteroides, Clostridium, Escherichia, Klebsiella, Leptospira, Micrococcus, Neisseria, Paracolobacterium, Proteus, Pseudomonas, Rhodopseudomonas, Sarcina, Serratia, Streptococcus* and *Streptomyces, Methanobacterium omelianskii, Mb. Formicium, Mb. Sohngenii, Methanosarcina barkeri, Ms. Methanica, Mc. Masei, Methanobacterium thermoautotrophicum, Methanobacterium bryantii, Methanobrevibacter smithii, Methanobrevibacter arboriphilus, Methanobrevibacter ruminantium, Methanospirillum hungatei, Methanococcus vannielli, Methanothrix soehngenii, Methanothrix sp., Methanosarcina mazei, Methanosarcina thermophila, Methanobacteriaceae, Methanosarcinaceae, Methanosaetaceae, Methanocorpusculaceae, Methaanomicrobiaceae,* other archaea and any combination of these.

In some embodiments, the microorganisms are from the genera of *Acetobibrio, Acitothermus, Actinobacillus, Anaerobiospirillum, Anaerocellum, Anaeromyces, Aspergillus, Basfia, Butyrivibrio, Caldicellulosiruptor, Cellulomonas, Cellvibrio, Corynebacterium, Cytophaga, Erwinia, Fibobacter, Fibrobacter, Mannheimia, Neocallimastix, Orpinomyces, Paenibacillus, Pectobacterium, Piromonas, Prevotella, Prevotella, Rhodothermus, Ruminococcus, Ruminococcus, Saccharophagus, Sorangium, Sphaeromonas, Thermobifida, Thermotoga, Wolinella,* and *Zygosaccharomyces.* The microorganisms may be from the order of Actinomycetales, or from the family of Pasteurellaceae.

As used herein, the term "microorganism consortium" refers to a microorganism assemblage, containing two or more species or strains of microorganisms, and especially one in which each species or strain benefits from interaction with the other(s).

In some embodiments, the microorganisms may be pure strains. In some embodiments, the microorganisms may be genetically modified organisms, especially in making biogas from carbonaceous materials.

As used herein, the term "oxygen carrier" refers to a metal oxide of a metal that has a first higher oxidation state and a second lower oxidation state, where the metal oxide containing the metal at the first higher oxidation state can release at least one oxygen atom when the metal in the metal oxide is reduced to the second lower oxidation state. The metal or metal oxide or mixed metal oxide containing the metal or metals at the second lower oxidation state may be subsequently oxidized to the metal oxide containing the metal at the first higher oxidation state. The metal oxide produced by the oxidation step is thus cable of carrying oxygen to a reaction where the oxygen may be released by reducing the metal in the metal oxide in order to provide oxygen for oxidizing a carbonaceous feedstock.

As used herein, the term "solubilizing" or "solubilized" refers to a process whereby the high molecular weight hydrocarbon molecules that comprise coal, lignocellulosic materials, or other carbonaceous material are reduced to much smaller hydrocarbon molecules or compounds by the application of one or more oxidizing agent that can cleave carbon bonds and other chemical bonds of the high molecule weight hydrocarbon molecules and react with the oxidizing agent to form smaller and water soluble hydrocarbon molecules that are then biologically converted to specific chemicals of interest and/or directed to the formation of biogas, a combination of methane, carbon dioxide and other useful gases. Solubilization for the purposes of the invention means the conversion of a solid carbonaceous material, such as coal or lignocellulosic materials, to a form of oxygenated carbon compounds that are in solution with water, and more specifically a form of oxygenated carbon compounds comprised of compounds that are soluble in water and capable of passing through a 0.45 micron filter.

As used herein, the term "substantially" means an amount of at least generally about 80%, alternatively at least about 90%, or alternatively, at least about 99%.

Referring to FIG. 1, the present invention provides a method for solubilizing a carbonaceous feedstock, comprising the steps of (a) reacting 100 a mixture of the carbonaceous feedstock with a metal oxide including a metal at a first, higher oxidation state to reduce the metal of the metal oxide to a second, lower oxidation state by releasing at least one oxygen atom from the metal oxide, which released oxygen atom can be used to oxidize the carbonaceous feedstock, and (b) oxidizing 200 at least a portion of the metal or metal oxide containing the metal at the second lower oxidation state to the metal oxide containing the metal at the first, higher oxidation state for reuse in reaction step 100. The method of the present invention can simultaneously oxidize, depolymerize, reform and/or solubilize high molecular weight, insoluble carbonaceous molecules in the carbonaceous feedstock to provide lower molecular weight hydrocarbons, oxo-chemicals and other chemicals. These relatively lower molecular weight products are soluble and biodegradable and may be further converted to valuable chemicals by microorganisms.

In some embodiments, the carbonaceous feedstock may be too impermeable, e.g. due to having a limited porosity, to be efficiently treated by the reaction step 100. In such a case, the carbonaceous feedstock may be preprocessed (e.g. comminuted) to increase its permeability or available surface area, thus increasing the susceptibility of the high molecular weight carbonaceous molecules in the carbonaceous feedstock to the treatment of the present invention. Any method known to a skilled person that is suitable for reducing the particle size of carbonaceous feedstock may be used in this step of the present invention. For example, physical (e.g., grinding, milling, fracture and the like) and chemical approaches (e.g., treating with surfactants, acids, bases, oxidants, such as but not limited to acetic acid, sodium hydroxide, percarbonate, peroxide and the like) can be applied to reduce the size of the particles of the carbonaceous materials in the carbonaceous feedstock. Some suitable preprocessing methods are described in, for example, US 2010/0139913, WO 2010/1071533 and US 2010/0262987, the disclosures of which are hereby incorporated by reference herein in their entirety.

In one embodiment, coal and water at about a 1:2 weight ratio are loaded into a mill with steel media. The duration of milling may be in the range from 60 to 90 minutes. After milling, the coal slurry may be used as the carbonaceous feedstock in the reaction step 100 of the process of the present invention.

The metal oxide functions as an oxygen carrier, which can take in, store and release oxygen for the oxidization of carbonaceous feedstocks. The metal of the metal oxide has at least two oxidation states: a first, higher oxidation state and a second, lower oxidation state. The metal oxide is selected for the ability of the metal in the metal oxide to switch between the two oxidation states. When the metal oxide is reduced from the first, higher oxidation state to the second, lower oxidation state, at least one oxygen atom is released from the metal oxide. The released oxygen atom(s) may be used to oxidize the carbonaceous feedstock. The metal or metal oxide including the metal at the second, lower oxidation state may be oxidized back to the first, higher oxidation state and may then be reused for oxidizing the carbonaceous feedstock. The metal oxide may be a mixture of two or more metal oxides. In some embodiments, the metal or metal oxide including the metal at the second, lower oxidation state may be the metal in its metallic state (such as Cu) and the metal oxide having the metal at the first, higher oxidation state may be a metal oxide (such as CuO). Utilization of metal oxide can lead to enhanced oxygen transfer via solid-solid contact and can also reduce or eliminate the need for a large-volume, gas-phase carrier of oxygen, either as pure oxygen or as air.

The metal oxide can be an oxide of a transition metal including metals of the lanthanide and actinide groups or a combination thereof. The lanthanide metals are rare-earth elements, having atomic numbers 57 through 71. The actinide metals extend from actinium (atomic number 89) or thorium (atomic number 90) through lawrencium (atomic number 103) on the periodic table. Examples of suitable metals include, but are not limited to, Fe, Ti, Cu, Ni, V, Cr, Mn, Co, Mo, La, Ce, Zr, Sr, W, Rh, Ba, Pt, Pd, Ag and so on. In some embodiments, Ni is selected as the metal in the metal oxide. In some embodiments, the metal oxide comprises more than one metal such as in the case of mixed metal oxides. The metal oxide may be in pure form or can be a mixture of two or more metal oxides in the list above, or the metal oxide may be modified or promoted by other metal oxides including oxides of alkali and alkaline earth metals.

In one embodiment, the metal oxide may be selected from several groups: (a) compounds having the formula $Ce_xB_yB'_zB''O_\delta$, wherein B=Ba, Sr, Ca, or Zr; B'=Mn, Co, or Fe; B''=Cu; $0.01<x<0.99$; $0<y<0.6$; $0<z<0.5$; and $1<\delta<2.2$; (b) compounds having the formula $Sr_vLa_wB_xB'_yB''_zO_\delta$, wherein B=Co or Fe; B'=Al or Ga, B''=Cu; $0.01<v<L4$; $0.1<w<1.6$; $0.1<x<1.9$; $0.1<y<0.9$; $0<z<2.2$; and $3<\delta<5.5$; (c) $Ce_{1-x-y}Ni_xB_y$ $O_{2-*}$, wherein B=Zr, Ba, Ca, La, or K; $0.02<x<0.1$; $0<y<0.1$; and $0.02<*<0.15$; (d) $M_{1-x-y}A_x(B)_yO_z$, wherein M=Co, Fe, or Mn; A=Ce, Zr, or both; B=La or Ca; $0.01<x<0.99$; $0.01<y<0.99$; $2<z<3.5$; and $(x+y)\leq 1$; (e) $AB_{1-x}B'_xO_y$, wherein A=Sr or Ba, B=Ce or Zr, B'=Y or Yb, and $0<x<0.5$, on a support comprising $MO_x$, wherein M=Ce, Mn, or Ni, or on a support comprising x % $MO_x/y$ % $A_2WO_4/(MgO$ or $SiO_2)$, wherein M=Ce, Mn, or Ni, and A=Na or K, $1\leq x\leq 3$, and $3<y<8$; (f) unary metal oxides selected from the group consisting of $Fe_2O_3$, $Fe_3O_4$, $MnO_x$ $CoO_x$, $NiO_x$, wherein $1\leq x\leq 2$, $CaCO_3$, $Ca(OH)_2$; and (g) binary metal oxides selected from the group consisting of $FeTiO_3$, $Mn_{1-x}CuO_2$, and $M_{1-x}Fe_xO_y$, wherein $0.01<x<0.99$, $1\leq y\leq 1.5$.

The weight ratio of the metal oxide to the carbonaceous feedstock in the reaction step 100 may depend on the characteristics of the carbonaceous feedstock and the properties of the metal oxide. In some embodiments, the weight ratio of the metal oxide to the carbonaceous feedstock is from about 0.1:100 to about 10:100, or from about 0.5:100 to about 5:100, or frons about 1:100 to about 3:100.

In some embodiments, the metal oxide may be on a thermally stable inert support. The support may be made from materials such as carbon, activated carbon, pumice, alumina, silica, silica-alumina, magnesia, diatomaceous earth, bauxite, titania, zirconia, clay, magnesium silicate, silicon carbide, zeolites, ceramics, carborundum, quartz, thoria, chromite, rutile, illmenite zircon, bauxite and combinations thereof.

Referring to FIG. 1, the thermally inert support may also function as a heat transfer medium, thereby improving the heating of the carbonaceous feedstock in reaction step 100. The support can absorb heat when the metal oxide and the support are heated 10, and may release the absorbed heat after the metal oxide/support is mixed with the carbonaceous feedstock and any other components. Release of the absorbed heat by the support will increase the temperature of the carbonaceous feedstock, thus facilitating oxidization and solubilization of the carbonaceous feedstock. Since the metal oxide with its support is mixed with the carbonaceous feedstock and other components, preferably homogenously, the support's function as a heat transfer medium can help to heat the carbonaceous feedstock more evenly and more quickly.

The heat transfer function of the support is determined by several properties of the support material, such as the specific heat and thermal conductivity. Specific heat determines the heat capacity of the support. Thermal conductivity determines the rate of heat release from the support. A person skilled in the art can select a suitable support material for the metal oxide for a specific application of the present invention. For example, if the carbonaceous feedstock prefers a quick heating to a preset temperature (e.g., to avoid producing byproducts at intermediate temperatures), the specific heat and thermal conductivity of the support material is preferably high.

The support for the metal oxide may be in variety of shapes, primarily designed to increase the contact surface between the metal oxide and the carbonaceous feedstock, allow easy separation and recovery in the process and limitation of pressure drop. In some embodiments, the support is in the form of small-sized particles or thin fibers. In other cases, the support may be selected from extrudates, monoliths, powder. The metal oxide on such a support will have a relatively large contact surface per unit weight of metal oxide. Such geometric shapes of the support can provide the following advantages:

provide the metal oxide with a high capacity (per unit of weight) to fix and release the oxygen, confer on the metal oxide a good mechanical strength, in particular against attrition, and promote the kinetics of the reaction between the metal oxide and the carbonaceous feedstock, and, subsequently with the oxidizing agent.

When the support is in particle form, the average particle size of the support does not typically exceed about 200 microns and is typically no greater than about 150 microns, or no greater than about 100 microns, or no greater than about 50 microns, or not exceeding about 20 microns. When the support is in the form of thin fibers, the fibers may have an average diameter of from about 1 micron to about 1 millimeter, and desirably from about 5 microns to about 20 microns, or from about 5 microns about 50 microns, or from about 5 microns about 100 microns, or from about 5 microns about 500 microns.

In some embodiments, the support is a monolith. The monolith may be in a variety of structural shapes. In one embodiment, the monolith is a honeycomb structure. Different compositions are contemplated for the monolith. In some embodiments, the monolith comprises ceramic material. In one embodiment, the ceramic material is cordierite. Optionally in addition to the ceramic material (e.g., cordierite) of the monolith, the monolith may also include additional components coated or blended therewith. For example and not by way of limitation, these additional components may include activated carbon, sulfur, other metal catalysts, binders, fillers, etc. In some embodiments, the monolith may comprise activated alumina, aluminum silicate, silica gel, titanium oxide, silicon carbide or mixtures of said materials, or sintered ceramics such as a Al2O3. In preferred embodiments, the monolith comprises mullite or cordierite.

In one embodiment, the monolith has a length of from a few centimeters up to about 20 cm and the cross-sectional size is usually smaller than 20 to 50 mm. The individual catalyst modules in the monolith support are spaced from each other by glass spheres, having a diameter of 3 to 6 mm.

In some embodiments, the monolith support is provided with channels that are substantially parallel to the longitudinal axis of the monolith. The perpendicular cross section of the channels, hereinafter designated as "cells", is delimited by a closed line, represented by the perimeter of the cross-section of the channels. Every regular or irregular shape of the cell perimeter can be used, the preferred ones being square, triangular, hexagonal and circular, since they are easy to manufacture. The cell density, i.e. the number of cells per unit cross sectional area of the monolith, is preferably at least 3 cells/cm$^2$, and more preferably between 8 and 100 cells/cm$^2$, in order to assure a sufficient geometric surface of the monolith walls to achieve the desired function.

The size of the cells, defined by means of the hydraulic diameter, i.e. four times the ratio of the cross sectional area to the perimeter of the cell, is generally less than 5 mm, preferably between 1 and 3 mm. This reduced size of the cells represents an advantage since it is possible to put more cells in the monolith per unit of cross-sectional area. Although the cells can be different from each other in size, a uniform size is preferred since this makes the monolith easier to manufacture.

The volume fraction of the monolith support is preferably less than 0.9, more preferably between 0.15 and 0.6. This reduced volume fraction of monolith support represents an advantage since it provides high monolith void fractions, thus further reducing pressure drops. Further, a reduced volume fraction of the support allows an important savings of expensive support material and a reduction of the reactor weight. The geometric surface area per unit volume of the monolith may be at least 6 cm$^2$/cm$^3$, preferably at least 10 cm$^2$/cm$^3$. The techniques for preparation of monoliths are well known. See for example X. Xu and J. A. Moulijn in "Structured Catalysts and Reactors", A. Cybuiski and J. A. Moulijn Eds., M. Dekker, New York, 1998, which is hereby incorporated by reference herein.

In some embodiments, the metal oxide and at least one binder may extruded by any process that is capable of producing extrudates, which extrudates are the resulting material that has been extruded through a die. Here, extruding or extrusion is the process of directing, generally using some type of mechanical force, a material through a die, for example, a metal die, typically, followed by cutting, cooling, and/or chemical hardening. Extrudates may have many shapes and may be distinguished by their shape. Examples of extrudates include but are not limited to pellet extrudates, cylindrical (solid or hollow) extrudates, trilobe extrudates, and quadrulobe extrudates, etc. In some embodiments, the extrudates are lobed particles comprising two or more lobes, alternatively, three, four, or more lobes. Here a lobe refers to any projecting part, for example, at least one rounded projecting part.

In one embodiment, the process for making extrudates is as follows. At least one metal oxide and at least one hinder are mixed using any suitable method, such as mulling or kneading. The mixing is generally carried out at a temperature in the range of from 1 to 200° C. but preferably at ambient temperature. The mulling or kneading may be performed under any pressure, such as 0.140 atmospheric pressure. Typically, the process lasts from 1 minute to 10 hours. The composition is usually made into a stiff dough for extrusion. If necessary, a solvent may be added to the composition. Suitable solvents include water, alcohols, ethers, esters, amides, aromatic solvents, halogenated solvents, and the like, and mixtures thereof. Typical solvents include water and alcohols. Water is the preferred solvent.

The composition is then directed to an extruder usually with a force applied, for example, a mechanical force provided by a screw. The composition is then pushed through a die or an orifice to create elongated objects of a fixed cross-section. The shape of the extrudates is dependent on the opening of the cross-section of the die or an orifice. Any conventional extruder may be used. The composition to be extruded may also include one or more extrusion aids. An extrusion aid helps the mixing, mulling, or extruding operation, and may improve the mechanical and/or physical properties of the extrudate such as the crush strength, surface area, pore size, and pore volume. Extrusion aids are well known and a listing of some extrusion aids including additional information may be found in, for example, WO 2008/088452, which is hereby incorporated by reference herein.

The extrudates may be dried and calcined before use in the present invention. The extrudates generally have an average particle size of 1.5875 mm (¹⁄₁₆th inch) or less or, alternatively, 1.2700 trim (1720th inch) or less. In another embodiment, the extrudates generally have an average particle size of 1.6 mm (about ¹⁄₁₆th inch) or less or, alternatively, 1.3 mm (about 1720th inch) or less. As used herein, "average particle size" of the extrudates refers to the arithmetic average of the diameter distribution of the extrudates, for example, weight based particle size. In some embodiments, the extrudates may have an average particle size of at least about 0.1 mm, 0.2 mm, 0.3 mm, 0.4 mm, or 0.5 mm up to and including about 1.3 mm, 1.5 mm, 1.6 mm, 2.0 mm, or 2.5 mm. Methods of measuring the size of extrudates are known and any suitable method may be used. Sieving, microscopy (e.g., electron microscopy), and laser techniques are some examples. For more information regarding the extrusion process and extrudates, see WO 2007/006398; WO 2008/088452; U.S. Patent Application Publication Nos. 2006/01.99987; 2009/0216056; and EP 0 220 933 A, the disclosures of which are hereby incorporated by reference herein.

The fibers may be organized into the form of meshes, webs, or nets. In one embodiment, a mesh-like support may comprise fibers of different materials, such as ceramic fibers and metal fibers. The mesh-like structure may comprise a single layer, or may include more than one layer. It may be made of a knitted or woven fiber structure and preferably comprises a plurality of layers of fibers to form a three-dimensional network of support materials.

In a preferred embodiment, where the mesh-like structure comprises a plurality of layers of fibers to form the three-dimensional network, the thickness of the support is at least about 5 microns, and generally does not exceed about 10 millimeters. In accordance with a preferred embodiment, the thickness of the network is at least about 50 microns but does not exceed about 5 millimeters, and more preferably is at least about 100 microns but does not exceed about 2 millimeters.

In one embodiment of the present invention, the mesh-like support structure may include tabs or vortex generators to cause turbulence in a liquid carbonaceous feedstock. The presence of the tabs or vortex generators enhances mixing in the radial (and longitudinal) direction and also improves access to metal oxide coated on the mesh by providing local pressure differentials across the mesh, thus creating a driving force for the flow of liquid carbonaceous feedstock.

The metal oxide may be coated on the fibers, extrudates, monoliths, powders, and mesh-like structures by a variety of techniques, e.g., dipping, spraying, and impregnating. In some embodiments, the metal or metal oxide may be applied to the mesh-like structure by contacting them with a liquid coating composition (preferably in the form of a coating bath) that includes the metal oxide particles dispersed in the liquid under conditions such that the coating composition enters or wicks into the mesh-like structure and forms a coating on both the interior and exterior surfaces of the mesh-like structure which coating may be porous. The metals or mixed metals may be deposited as solubilized forms of the metals, such as salts dissolved in water. Nitrates are typically used, but so are chlorides and other compounds. After deposition and drying, the metals are converted to oxides in an air calciner.

At least some components of the carbonaceous feedstock are oxidized by the at least one oxygen atom released from the metal oxide. The oxidization step breaks down high molecular weight molecules in the carbonaceous feedstock to lower molecular weight hydrocarbons, oxo-chemicals and other chemicals, which are water soluble and biodegradable.

In some embodiments, at least one oxidizing agent is optionally added to reaction step 100 for oxidizing the carbonaceous feedstock. The oxidizing agent may be selected from air, oxygen-enriched air, oxygen, ozone, sulfuric acid, permanganates, carbon dioxide, nitrous oxide, nitric acid, chromates, perchlorates, persulfates, superoxides, chlorates, peroxides, hypochlorites, Fenton's reagent and nitrates in which the cations may comprise metal cations, hydrogen ions and/or ammonium ions. Air and oxygen-enriched air are the preferred oxidizing agents. One goal of the present invention is not to over-oxidize the carbonaceous feedstock. Therefore, the type, amount and rate of addition of the oxidizing agent being used should be consistent with this goal. In some embodiments, the oxidizing agent is used to rejuvenate the metal oxide catalyst which in turn transfers oxygen more selectively to the carbonaceous feedstock than by, for example, direct transfer of the oxygen from the oxidizing agent. This may be achieved by separated steps of loading the metal oxide catalyst with oxygen and unloading oxygen into the carbonaceous feedstock from the metal oxide; or by going through periods of metal oxide catalyst regeneration followed by reaction with the carbonaceous feedstock.

To prevent over-oxidation of the carbonaceous feedstock, the strength of the oxidizing agent needs to be considered. Oxidizing agents may be ranked by their strength. See Holleman et al. "Inorganic Chemistry," Academic Press, 2001, page 208. A skilled person will appreciate that, to prevent over-oxidation of the carbonaceous feedstocks, the conditions in the reaction step 100 may be adjusted according to the strength of the oxidizing agent used. For example, when a strong oxidizing agent is used, one or more of temperature, pressure, and duration of the reaction step 100 may be reduced to prevent over-oxidation and/or ensure that the desired degree of oxidation is not exceeded. On the other hand, when a weak oxidizing agent is used, one or more of temperature, pressure, and duration of the reaction step 100 may be increased to ensure that the desired degree of oxidation is achieved. When the oxidizing agent is gaseous, the pressure used for the reaction step 100 is important for ensuring the desired degree of oxidation for the carbonaceous feedstock.

In some embodiments, oxygen is used as the oxidizing agent. In one embodiment, oxygen is provided in air. In some other embodiments, depending on the susceptibility of the carbonaceous feedstock to oxidation, oxygen-enriched air can be used. Suitable enrichment percentages can provide an oxygen concentration slightly above that of atmospheric air to substantially pure oxygen.

In some embodiments, heated steam may be introduced into the reaction in reaction step 100 for providing heat to the mixture. The steam may also be used for fluidization, acceleration, and transport of the carbonaceous feedstock and metal oxide. The reaction step 100 may comprise raising the temperature of a mixture of the carbonaceous feedstock and metal oxide to a desired temperature by providing heated steam to a reaction vessel housing the mixture. The heating of the mixture in a closed container may also subject it to a pressure at or above the steam saturation pressure. Multiple reactions may occur during the reaction step 100, including oxidization, depolymerization, reforming and solubilization. In a reforming process, the molecular structure of a hydrocarbon is rearranged.

In some embodiments, the reaction step 100 is performed at a temperature below about 300° C. (572° F.), or below about 220° C. (428° F.), or below about 170° C. (302° F.). In preferred embodiments, the temperature is in a range of from about 140° C. to about 270° C., or from about 200° C. to about 220° C. The reaction step 100 may also be performed under a positive pressure at saturated steam pressure or slightly higher, for example below about 1230 psia, or below about 1000 psia, or below about 900 psia respectively. In preferred embodiments, the pressure is in a range of from about 200 psia to about 1230 psia, or from about 500 psia to about 1000 psia or from about 700 psia to about 900 psia.

The reaction time for the reaction step 100 can vary from about 1 minute to about 5 hours, or from about 1 minute to about 2 hours, or from about 1 minute to about 1 hour, or from about 5 minutes to about 30 minutes. The present invention may be performed within a large range of pH, not limited to any particular acidic or basic pH range. This is advantageous relative to previous methods because many such methods are subject to pH restrictions.

The reaction conditions in reaction step 100 including temperature and pressure may depend on molecular and elemental characteristics of the particular carbonaceous feedstock to be solubilized. Examples of the characteristics of the carbonaceous feedstock which may be taken into consideration are its degree of aromaticity, hydrogen to carbon ratio, oxygen to carbon ratio, nitrogen to carbon ratio, sulfur to carbon ratio, mineral or ash content, and other factors. Thus, in some embodiments, a blend of carbonaceous feedstocks of different characteristics may be used to enhance the efficiency of the present invention by adjusting one or more of these characteristics. For example, blending a highly aromatic (more difficult to oxidize) carbonaceous material, such as coal, with a more acyclic carbonaceous material, such as agricultural waste or synthetic polymer waste, may result in an oxidized product stream that is more biodegradable and may support greater microbial population densities, as well as potentially increasing the rate and depth of conversion of less reactive molecules in the feedstock. Blending techniques for providing the carbonaceous feedstock are described, for example, in US 2012/0160658, the disclosure of which is hereby incorporated by reference herein in its entirety.

The duration of the reaction step 100 may be determined, for example, by the oxidative stress induced in the reaction and/or the desired reaction products. As a general rule, a higher oxidative stress requires a shorter duration for the reaction step to avoid over-oxidation of the carbonaceous feedstock. In addition, if the desired products are generated by more complete oxidization of the carbonaceous feedstock, e.g. via a series of sequential reaction steps, a longer duration for the reaction step 100 may be required. The desired products of reaction step 100 may be determined by the degree of conversion required, the reduction in molecular weight desired, the reactivity of the feedstock, process economics, the amount of carbon dioxide, carbon monoxide and/or hydrogen generated, and other constraints.

The degree of oxidation (oxygen insertion in the carbonaceous materials) relative to carbon rejection as carbon dioxide or carbon monoxide) of the carbonaceous feedstock can be controlled by using different reaction conditions to yield different types and amounts of, for example, partial oxidation products. The reaction conditions may also be adjusted to eliminate or reduce insoluble coal or lignocellulosic material solids, other than inorganics concentrated in an ash stream, preferably without significant loss of carbonaceous compounds to $CO_2$.

The reaction step 100 of the present invention can generally solubilize the insoluble high molecular weight carbonaceous molecules in the carbonaceous feedstock without using a solubilizing agent. But in some embodiments, a solubilizing agent can be optionally used in the reaction step 100. If a solubilizing agent is used, the solubilizing agent may be selected from mineral acids or mineral bases. Preferred bases include Group I (alkali metal) and Group II (alkaline earth metal) oxides, hydroxides, carbonates, borates, or halogenates. In particular, sodium, potassium, calcium, and magnesium compounds are preferred. Examples of suitable solubilizing agents include sodium hydroxide, potassium hydroxide, ammonium hydroxide, sodium carbonate, sodium bicarbonate and potassium carbonate, or any mixture of these. Naturally occurring minerals of some of these materials are also appropriate for use in this process. These include, but are not limited to Nahcolite, Trona, Thermonatrite, Gaylussite, Hydromagnesite, Lansfordite, Hydrocalcite, Dolomite, Huntite, Aragonite, Natrite, Magnesite, Calcite, Kalcinite, Gregoryite, and others.

The mineral bases generally comprise no more than 15 wt % of the mixture provided to the heating step, and preferably comprise below 10 wt % and most preferably at or below 6 wt % of the mixture provided to the heating step. In some embodiments, the solubilizing agent comprises at least 1 wt % or at least 3 wt % or at least 5 wt % of the mixture fed to the heating step. In some embodiments, the solubilizing agent may be a mineral acid, such as phosphoric acid, nitric acid, boric acid, hydrochloric acid, and sulfuric acid. The solubilizing agent may also be an organic acid, such as acetic acid or formic acid, which may be produced in the coal oxidization process. Thus, in some embodiments, organic acids produced by the process of the present invention may be separated and introduced back to the process as a solubilizing agent to accelerate the conversion of the carbonaceous feedstock, in particular the conversion to celluloses from lignocellulosic materials.

The carbonaceous feedstock may be mixed with the solubilizing agent provided in an aqueous solution to make the mixture with metal oxide. In some alternative embodiments, the carbonaceous feedstock may be combined with steam or water vapor containing the solubilizing agent. In these embodiments, the vapor or steam may be blown onto the carbonaceous feedstock.

The amount of carbonaceous feedstock dispersed in the aqueous solution is determined, to some extent, by factors such as the average size of the polymeric molecules in the carbonaceous feedstock and their solubility in water which may be based on the functional groups of the carbonaceous materials, the degree of ionization of the carbonaceous materials in water, and physical and chemical attributes of the aqueous system, such as temperature, pH, pressure, activity coefficient, and other considerations. Solution viscosity also increases with higher carbonaceous feedstock loading in the slurry-like mixture and is a limitation that may reduce mass transfer and mixing between the solid metal oxide and carbonaceous feedstock in the liquid.

In some embodiments, the carbonaceous feedstock content in the mixture may be less than about 40% by weight. In other embodiments, the carbonaceous feedstock content of the mixture may be at or below about 30% by weight or at or below about 25% by weight.

In the present invention, the metal oxide functions as an oxygen carrier for the oxidation/solubilization of the carbonaceous feedstock. In some embodiments, a catalyst may optionally be added to the reaction step 100. This catalyst may catalyze the oxidation reaction by, for example, causing or enhancing formation of peroxides and superoxides, which may in turn enhance the rate of oxygen insertion into the carbonaceous molecules in the carbonaceous feedstock. The catalyst may be selected from water insoluble metals, transition metals, and precious metals, and salts thereof. Examples of these metals include nickel, cobalt, platinum, palladium, rhenium, copper, vanadium, zirconium and ruthenium. The catalyst may be unsupported or may be supported on inert or active matrix material such as clay, alumina, silica, silica alumina, zeolites, activated carbon, diatomaceous earth, titania, zirconia, molybdena, ceramics, and the like. Such catalysts can enhance rates of oxygen transfer, oxygen insertion and reforming of high molecular weight carbonaceous compounds as well as being able to enhance the degree of relative oxidation. Examples of the catalysts include hydroxides, carbonates, ceria, lanthanum, mixed rare earths, brucite, hydrotalcite, iron, clays, copper, tin, and vanadium.

In some embodiments, the catalyst is a solid catalyst containing activated carbon. The type of activated carbon suitable for use as a catalyst in the present invention is not specifically limited. Suitable activated carbons may be selected from materials such as charcoal, coal, coke, peat, lignite and pitch. Suitable activated carbons may also include carbon fibers, such as activated carbon fibers of the acrylonitrile family, the phenol family, the cellulose family, and the pitch family.

Activated carbon can adsorb oxidizable substances from the carbonaceous feedstock onto its surface. The adsorption of oxidizable substances onto the catalyst surface creates chemical bonding, altering the electron density around the molecules of the oxidizable substance and allowing the molecules to undergo oxidation with higher efficiency. For the purpose of catalyzing the oxidation reactions, the type and amount of polar groups on the surface of the activated carbon can change the properties of activated carbon. The amount or type of polar groups on the surface of the activated carbon affects the formation of chemical bonds with oxidizable substances. Thus, the performance of the activated carbon as a catalyst changes considerably in accordance with the amount and type of polar groups introduced into the catalyst. If the oxidizable substances are mostly organic substances and/or inorganic anionic substances, the activated carbon catalyst may contain a small amount of polar groups, which give the catalyst hydrophobic properties for more efficient catalysis of oxidation. The activated carbon catalysts suitable for oxidizing large organic substances are described in more detail in European patent no. 1 116 694 B1, the disclosure of which is hereby incorporated by reference herein for the purpose of describing use of activated carbon catalysts for oxidizing large organic substances.

The amount of the polar groups on the surface of activated carbon may be controlled by varying the process of producing the activated carbon catalyst. For example, U.S. Pat. No. 3,996,161 describes a method of preparing active carbon for treatment of waste liquid comprising immersing powdered coal in an aqueous solution of a polar compound containing a non-polar group bonded to a polar group, and then washing the immersed coal followed by drying of said washed coal. This document is hereby incorporated in its entirety by reference herein. By varying the polar compound or its amount in the aqueous solution, activated carbon with different amounts of polar groups may be produced.

The reaction step 100 of the present invention may be performed in a reaction vessel. The reaction vessel is not limited to any particular design, but may be any sealable reaction vessel that can tolerate the temperature and pressure required for the present invention. In some embodiments, the mixture of carbonaceous feedstock and metal oxide, as well as any other components, is fed to the reaction vessel, which has been pre-heated to the desired temperature. Then, air or oxygen enriched air may optionally be added to the reaction vessel until the desired pressure is reached. The temperature and pressure in the reaction vessel may be monitored during the filling of air or oxygen enriched air, as well as during the reaction step itself. Some suitable reaction vessel designs are described in Blume ("Bitumen blowing unit converts residues to asphalt," *Hydrocarbon Processing*, March 2014), which is hereby incorporated by reference herein.

In some embodiments, the mixture in the reaction vessel has at least two phases: a liquid phase (water/solubilizing agent/oxidizing agent) and a solid phase (carbonaceous feedstock). In many embodiments, there are three phases in the reaction vessel: gas (oxygen/air and/or steam), liquid (water/solubilizing agent) and solid (carbonaceous feedstock and metal oxide). To ensure efficient heat and mass transfer among these phases, the mixture may be subjected to mechanical or other means of agitation. The reaction vessel may include structural features to facilitate interactions among the phases, for example, an unstirred reaction vessel may be provided with gas dispersion features, a reaction vessel may be provided with mechanical agitation devices and reaction vessels with gas entrainment devices may be used.

In the process of the present invention, there are two oxygen mass transfer steps which offer some flexibility for the production of secondary products, reducing activation energies and permitting lower thermal attack. The thermal attack, if not controlled/lowered, may over accelerate secondary oxidation where the small molecules (solubilized) produced by the process of the present invention are further oxidized to $CO_2$ or CO. This will lead to loss of carbon in the carbonaceous feedstock to $CO_2$ or CO. In one embodiment, the amount of oxidizing agent (such as air) in the reaction vessel is sufficiently small to ensure that more oxygen comes from the metal oxides in the reaction vessel.

Figure 4:
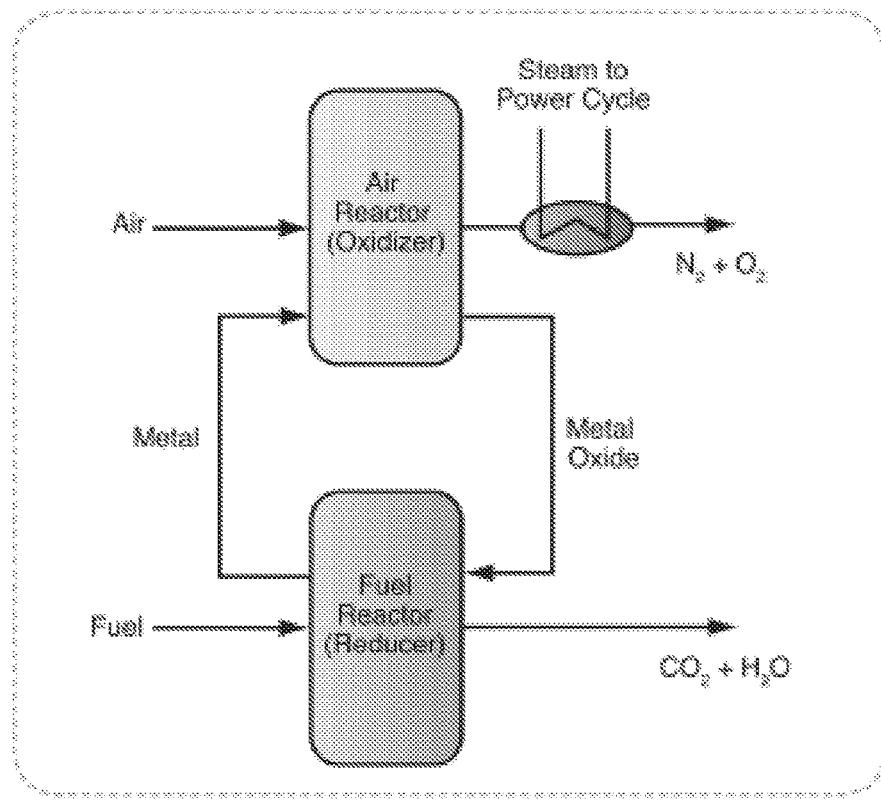
FIG. 4 is a schematic representation of a full combustion method known as chemical looping that recovers concentrated $CO_2$ from full combustion of a fuel.

In one embodiment, in which air is used for regenerating metal oxide to a higher state, the resultant oxygen depleted air from the regeneration step may be introduced into the reactor as the oxidizing agent. Such air, with the oxygen partially depleted, has a low oxygen partial pressure. Since rates of secondary reaction are proportional to oxygen partial pressure, the air with low oxygen partial pressure would reduce the rates of some secondary reactions, thus reducing the potential for carbon loss to $CO_2$ and CO production. This is different from a full combustion method, known as chemical looping that allows recovery of concentrated $CO_2$ from full fuel combustion (FIG. 4). In this combustion process, oxygen is carried into the combustion chamber by the catalyst after it is fully oxidized in air. Nitrogen exits the regenerator and thus does not dilute $CO_2$ exiting the combustion chamber after the fuel is combusted with the fully oxidized catalyst in the combustion chamber. This chemical looping combustion process resembles a poor man's air separation unit, where oxygen from the air is absorbed by the catalyst and carried to the combustion chamber while the nitrogen in the air is separated from the oxygen and discarded before it reaches the combustion chamber.

In some embodiments where oxygen in a gas (such as air) is introduced as the oxidizing agent, the reaction vessel is a bubble column reactor configured to enhance mass transfer of oxygen from the gas phase to the liquid phase. The bubble column reactor typically consists of vertically arranged cylindrical columns. Bubble columns are configured such that gas, in the form of bubbles, is introduced to a lower portion of the column and rises in the liquid phase. The introduction of gas to the reactor causes a turbulent stream to enhance oxygen transfer to the liquid phase as the bubbles rise to the top surface of the liquid phase. In this manner, the interaction between the gas and liquid phases is enhanced using significantly less energy than would be required for mechanical stirring. The liquid phase can be in parallel flow or counter-current flow with the gas phase. The gas escaping from the top surface of the liquid phase may be recycled back to the bubble column reactor and reintroduced back to the bottom of column.

The bubble column reactor can facilitate chemical reactions in a multi-phase reaction medium because agitation of the reaction medium is provided by the upward movement of gas bubbles through the reaction medium. The diameter of the bubbles can be correlated with the efficiency of gas-liquid mass transfer, since the bubble size has a strong influence on hydrodynamic parameters such as bubble rise velocity, gas residence time, gas-liquid interfacial area and the gas-liquid mass transfer coefficient. A person skilled in the art may determine the optimal size or size distribution of the bubbles for achieving efficient oxidation/depolymerization of the carbonaceous feedstock. Because different types of carbonaceous feedstocks have different characteristics, the size of the bubbles may be adjusted depending on the characteristics of the carbonaceous feedstocks and the desired oxidation products.

In some embodiments, the reaction vessel is an ebullating bed. In an ebullating bed a liquid is used to fluidize the metal oxide catalyst. Small catalyst fragments from the catalyst bed that are entrained in the liquid can be removed. The processed liquid can then be returned to the ebullating bed. In this manner, small fragments of catalyst will not be present in fluid above the ebullating bed and will thus prevent pump clogging when the liquid is recirculated.

In some other embodiments where oxygen in a gas (such as air) is introduced as the oxidizing agent, the reaction vessel is a trickle bed reactor configured to enhance mass transfer of oxygen from the gas phase to the liquid phase. In a trickle bed reactor, the liquid phase and gas phase flow in a co-currently flow downwardly through a fixed bed of metal oxide particles on which the reaction takes place. At sufficiently low liquid and gas flow rates, the liquid trickles over the metal oxide packing in essentially a laminar film or in rivulets, and the gas flows continuously through the voids in the bed. The maximum contact efficiency is attainable with high liquid mass velocities, e.g. 1-8 kg/m$^2$, or 2-5 kg/m$^2$. A detailed description of trickle bed reactors and other multi-phase reactors can be found under the heading "Reactor Technology" in "Kirk-Othmer Encyclopedia of Chemical Technology", Third Edition, Volume 19, at pages 880 to 914, the disclosure of which is hereby incorporated by reference herein for the purpose of describing these reactors in more detail.

Trickle bed reactors may be operated in various flow regimes, depending on vapor and liquid flow rates and properties. The operating window of trickle flow is very wide and not only determined by flow rates (see, e.g., E. Talmor, *AIChE Journal*, vol. 23, pages 868-874, 1977, which is hereby incorporated by reference herein). Thus, in some embodiments, it may be possible to operate the trickle bed reactor with low liquid flow rates in conjunction with relatively high gas flow rates.

Some of the carbonaceous molecules in the feedstock may be oxidized to carbon dioxide. The $CO_2$ formed during the reaction has several roles, including acting as an excess base neutralizer and forming a carbonate buffering system in the reaction mixture. A carbonate buffered system is a desirable feature for enhancing the subsequent microbial conversion to gas and chemicals. In many cases, microbes of interest prefer a system at or around pH 7. The $CO_2$ produced in the reaction can react with excess base the thereby reduce or eliminate the need to adjust the pH of the product stream resulting from reaction step 100 by the addition of acid, thereby lowering costs for the reaction. The $CO_2$ also retains some of the mineralized carbon in the system, some of which can be reduced by certain microbes to beneficial products during metabolism of the solubilized carbonaceous feedstock. Any excess $CO_2$ formed during the reaction is preferably removed from the reaction vessel. In one embodiment, gas is withdrawn from the reaction vessel, the carbon dioxide content of the withdrawn gas is reduced and the gas with the reduced carbon dioxide content is optionally resupplied back to the reaction vessel, with or without being enriched with oxygen. This embodiment may be used for maintaining a desired partial pressure of oxygen in the reaction vessel during the reaction step 100.

Therefore, in some embodiments, it may be desirable to use a sufficiently alkaline solution to fix some, most or all of the carbon dioxide generated during the reaction step 100 to maintain a higher level of partial pressure of oxygen in the reaction vessel when the oxidizing agent is oxygen or oxygen-enriched air. Otherwise, the formation of carbon dioxide in the reaction vessel may reduce the partial pressure of oxygen in the system to a point where the oxidization reaction will slow down and eventually cease.

In some embodiments, the gas phase in the reaction vessel may be periodically sampled in order to monitor the progress of the reaction. The gas sample may be analyzed by, for example, a gas chromatograph to identify the content of one or more components to provide an indication of the progress of the reaction. Once the desired degree of conversion is reached, the reaction step 100 may be terminated. Carbon dioxide may be withdrawn or oxygen may be periodically or continuously added to the reaction vessel in order to maintain the desired level of oxidant.

The method of the present invention can be conducted in batch, semi-batch, or continuous modes. In one aspect, the present invention oxidizes high molecular weight carbonaceous molecules in the carbonaceous feedstock. At least portion of the carbonaceous molecules may be oxidized to organic acids, such as oxalic acid, mellitic acid, benzoic acid and acetic acid. In addition, the carbonaceous molecules may be depolymerized/reformed to lower molecular weight compounds. In some embodiments, mineral bases are used to increase the pH of the mixture to a caustic alkaline pH of greater than about 7, greater than about 9 or greater than about 10. In some embodiments, an acidic or approximately neutral pH, e.g. 6-8 or 6.5-7.5, may be used, which may not require the use of mineral base for pH adjustment. In such mixtures, the formed organic acids will be present in salt form if a mineral base is present as a component of the solubilizing agent. Such salts may be recovered from the reaction products by filtering off the solid material and extracting the oxalic acid therefrom with dilute hydrochloric or sulfuric acid. The salts of mellitic acid and like acids can be isolated from the filtrate by acidifying, warming, and filtering the warm liquid, while acetic acid can be recovered from the residual liquid by, for example, steam distillation.

The products from the reaction step 100 may include minerals and inorganic chemicals in addition to low-molecular weight carbonaceous compounds. These products may be used as raw materials for various industries such as the chemical, polymer, textile, and pharmaceutical industries. Metals may be recovered from the reaction product. The solids in the reaction vessel may also have value as a fertilizer, fillers for cement and asphalt, and other such materials.

In the reaction step 100, metal oxide is reduced to a lower oxidation state, which may be retrieved from the reaction mixture of reaction step 100 by separating the reduced metal oxide from a mixture of carbonaceous feedstock and any oxidation products. In some embodiments where the metal oxide is on a thermally inert support. the reduced metal oxide can be retrieved by removing the support from the reaction mixture. For example, particles can be separated from the other components in the mixture by physical separation, for example in a cyclone. The fibers or mesh can be retrieved from the mixture by any method known to a skilled person, such as filtering or sifting.

In oxidizing step 200 of the present invention (FIG. 1), at least a portion of the retrieved metal or metal oxide, which is reduced to a lower oxidation state in reaction step 100, is oxidized. The oxidization of the metal or metal oxide restores the metal of the metal oxide back to the higher oxidation state while introducing oxygen thereto. The produced metal oxide is thus ready to be reused in reaction step 100. In some embodiments, the oxidization 200 of the metal or metal oxide is performed at a location other than where reaction step 100 is performed. The oxidation 200 may be carried out using an oxygen containing gas, such as air or oxygen enriched air. On contacting with this oxygen containing gas, the metal in the metal or metal oxide is oxidized to the higher oxidation state by absorbing oxygen into the metal or metal oxide. This step can be carried out in several increments and/or with a sufficient residence time, and/or with an excess of oxygen-containing gas, until a desired degree of oxidization of the metal or metal oxide is obtained.

In some embodiments, in oxidizing step 200, the oxygen-containing gas may comprise between about 22% and about 100% of oxygen by volume. The other components in the gas are selected so as not to react with the metal or metal oxide, and may include nitrogen, argon, $CO_2$, and the like. In one embodiment, the reduced metal oxide can be brought into contact with several oxygen-containing gases, including air and other gases comprising between about 22% and about 100% of oxygen by volume.

Figure 2:
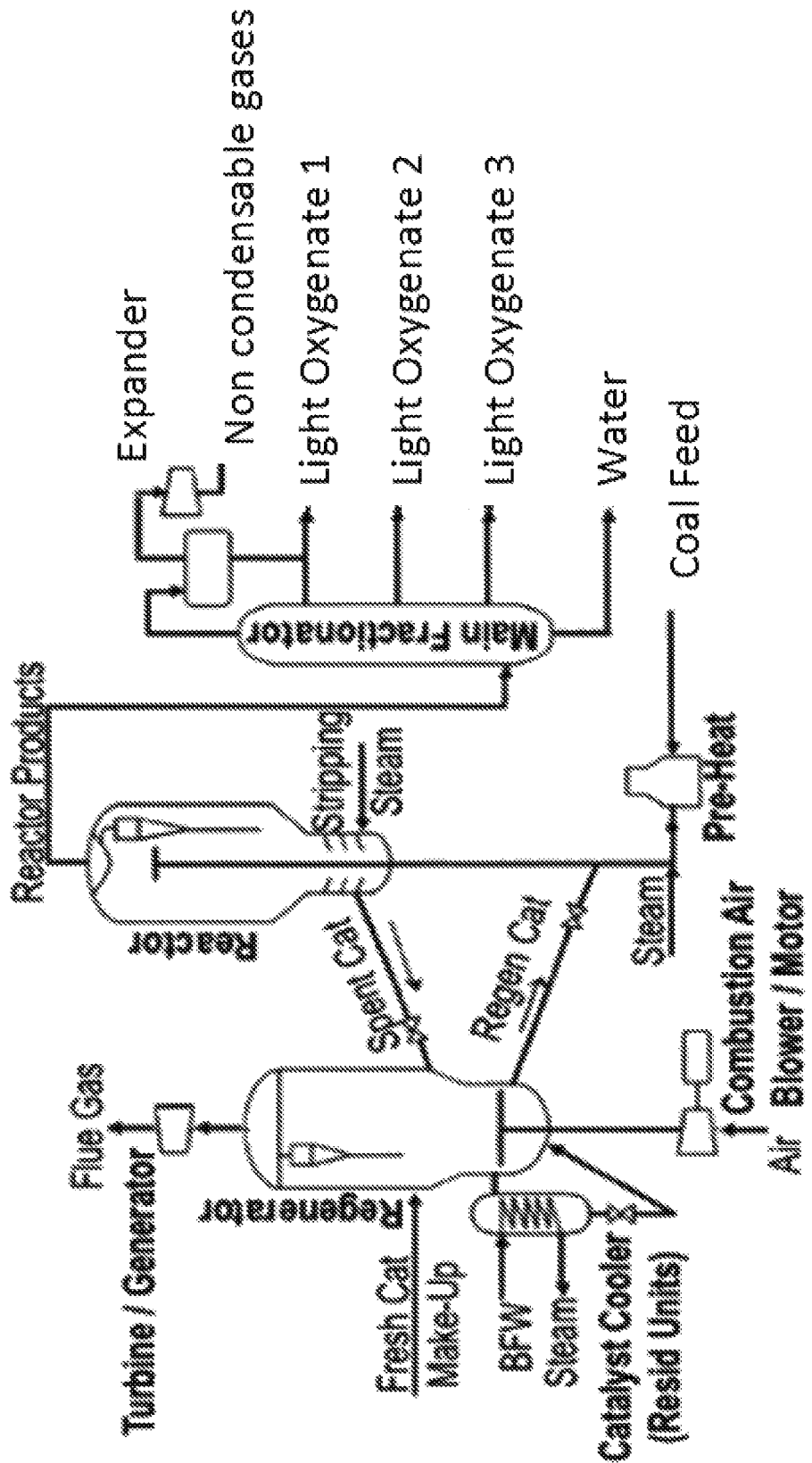
FIG. 2 is a diagram showing an apparatus that may be used for performing one embodiment of the method of the present invention.

In one embodiment, the present invention is implemented in an apparatus as shown in FIG. 2, which mimics a fluid catalytic cracking (FCC) cracker used for petroleum conversion. The apparatus comprises a reactor and a regenerator. Coal is used as the carbonaceous feedstock, which is mixed with heated steam and metal oxide in the reactor. The metal oxide is reduced from a higher oxidation state to a lower one (e.g. $CeO_2$ to CeO) in the reactor, delivering oxygen atoms to the carbonaceous feedstock. The released oxygen atoms perform oxidative cracking and oxygen insertion to the high molecular weight carbonaceous molecules in the feedstock. The used metal or metal oxide is retrieved from the reactor and placed in the regenerator, where air comes into contact with the metal or metal oxide to oxidize the metal to the first, higher oxidation state. Referring to FIG. 1, the oxidized metal oxide is recycled 300 back to the reactor, possibly supplemented by fresh metal oxide. The products from the reactor may be processed by a fractionator to separate the components in the products.

More specifically, condensable and non-condensable products of reaction step 100 may be separated from the metal oxide and partially solubilized coal particles using a series of cyclones. The cyclones may be directly or indirectly attached to the end of the reactor. Used metal or metal oxide and some coal particles are then transferred to the regenerator where contact with air causes complete combustion of the coal particles, while the used meal or metal oxide is oxidized and heated. The oxidized metal oxide is returned to the reactor. The oxidizing step 200 may be repeated many times in an hour. Condensable and non-condensable vapors containing carbon dioxide, water, and condensable oxygenate vapors are transferred from the effluent of the cyclones to a separation section where they are condensed in the case of condensable products, or sent to an expander in the case of non-condensable products, for recovery.

In some embodiments, it may be desirable to conduct the reaction step 100 as multiple sequential steps (100*a*, 100*b* in FIG. 5) in order to better achieve the desired degree of solubilization of the carbonaceous feedstock. The present invention thus encompasses methods wherein two or more sequential reaction steps 100*a*, 100*b* are conducted under different conditions using the reaction product of a previous reaction step as the feed to the following reaction step. The reaction conditions at each reaction step 100 a, 100*b* may be adjusted to favor different reactions, rates of reaction, degrees of conversion, etc.

For example, if a first reaction step 100*a* has its conditions optimized for higher biodegradability, additional solubilization of the carbonaceous feedstock may be desirable using a second reaction step 100*b* with different conditions. In another example, one reaction step 100*a* may have reaction conditions selected for the production of oxo-chemicals and another reaction step 100*b* may have its reaction conditions selected for enhancing biodegradability of the reaction products.

Alternatively, the reaction products of a previous reaction step 100*a* may be processed in some way before feeding them to the following reaction step 100*b* by, for example, chemically or physically separating one or more components of the reaction product. Also, the reaction products or one or more components thereof may be recycled back to the initial reaction step 100*a* under the same conditions. An additional pass through the reaction step 100*a*, 100*b* can be used to enhance or complete conversion and/or solubilization of the carbonaceous compounds in the carbonaceous feedstock. For example, remaining solids from a first reaction step 100*a* can be recycled back to the initial reaction step 100 after being separated by mechanical means. Filtering, settling, centrifuging, hydrocycloning and other techniques may be used to separate solids from the products of the reaction step 100*a*.

Figure 5:
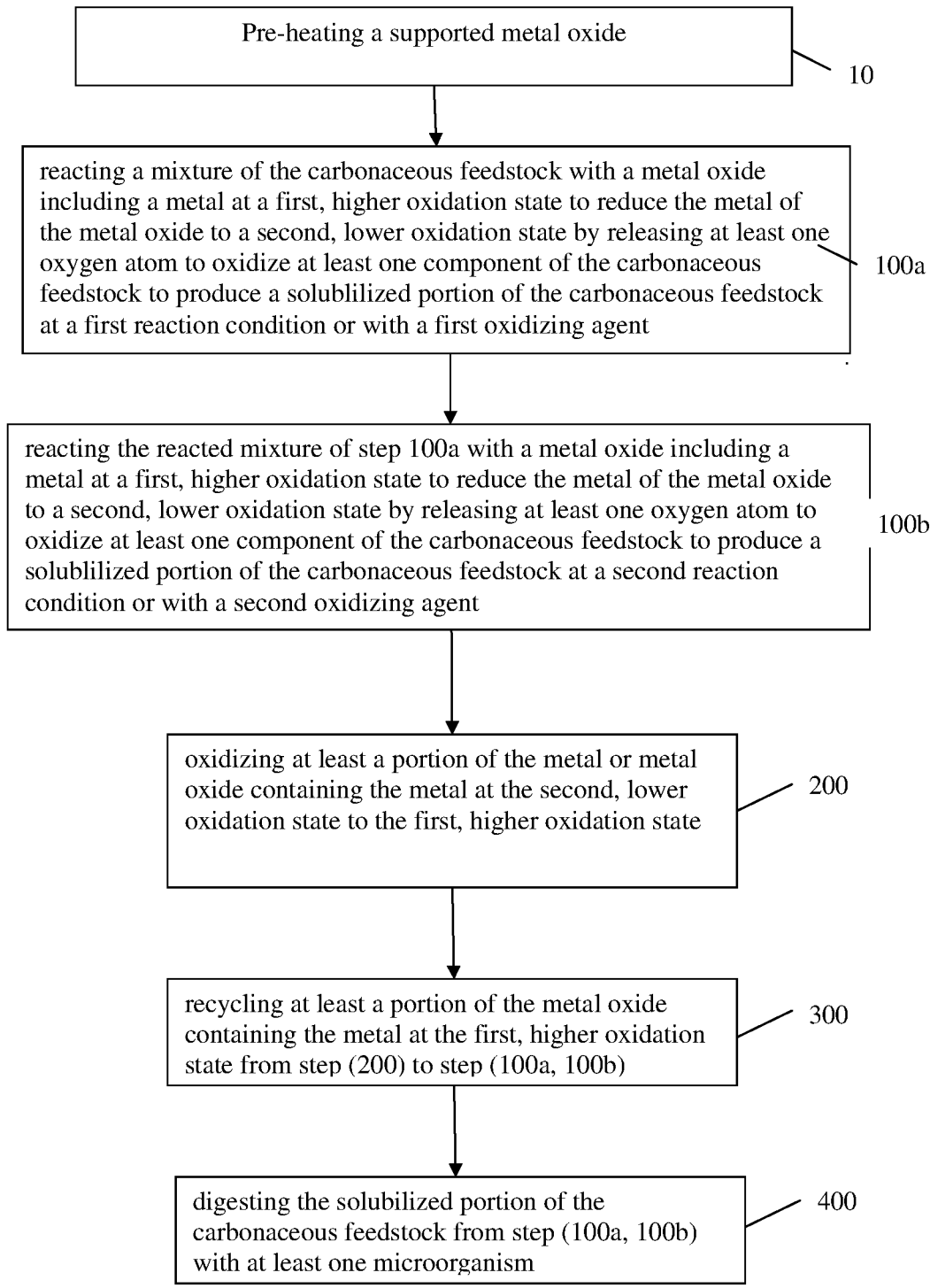
FIG. 5 is a flow chart showing an alternative embodiment of the present invention where the reacting step 100 in FIG. 1 may be configured as sequential reacting steps.

In the embodiment shown in FIG. 5, the method comprises the same steps as described in FIG. 1, except that the reacting step of FIG. 1 is implemented as multiple sequential steps (100*a*, 100*b*) in the method of FIG. 5. More specifically, the method of this embodiment comprises an optional initial step of pre-heating 10 a supported metal oxide. A mixture of the carbonaceous feedstock is then reacted 100*a* with metal oxide including a metal at a first, higher oxidation state to reduce the metal of the metal oxide to a second, lower oxidation state by releasing at least one oxygen atom to oxidize at least one component of the carbonaceous feedstock to produce a solublilized portion of the carbonaceous feedstock at a first reaction condition or with a first oxidizing agent. The mixture from step 100*a* is then further reacted 100*b* with a metal oxide including a metal at a first, higher oxidation state to reduce the metal of the metal oxide to a second, lower oxidation state by releasing at least one oxygen atom to oxidize at least one component of the carbonaceous feedstock to produce a solublilized portion of the carbonaceous feedstock at a second reaction condition or with a second oxidizing agent. At least a portion of the metal or metal oxide containing the metal at the second, lower oxidation state is then oxidized 200 to the first, higher oxidation state. At least a portion of the metal oxide containing the metal at the first, higher oxidation state is recycled 300 from step 200 to one or both of steps 100*a*,

100b. Finally, the method may include an optional further step of digesting 400 the solubilized portion of the carbonaceous feedstock with at least one microorganism.

The identity and amounts of small organic compounds in the reaction product depends on the reaction conditions including the pressure, and reaction temperature, the type and amount of metal oxide used, and the weight ratios of the metal oxide to the carbonaceous feedstock, as well as other factors such as the use of optional additional oxidizing agents, catalysts, etc. The reaction product from the reaction step 100 may include oxygenated hydrocarbons such as alcohols, aldehydes, carboxylic acids, salts of carboxylic acids, esters, ethers and anhydrides. Oxygenated compounds may be mono-functional, di-functional, trifunctional, or polyfunctional. The oxygenated hydrocarbons with more than one functional group include polyols, dicarboxylic acids, triacids, polyesters, polyethers and aldehydic acids, and other products.

Examples of carboxylic acids include compounds of the formula R—COOH, wherein R is an alkyl group. Particular examples include formic acid, methanoic acid, acetic acid, ethanoic acid, propionic acid, butyric acid, butanoic acid, valeric acid, pentanoic acid, caproic acid, hexanoic acid, enanthic acid, heptanoic acid, caprylic acid, octanoic acid, pelargonic acid, nonanoic acid, capric acid, decanoic acid, undecylic acid, undecanoic acid, lauric acid, dodecanoic acid, tridecylic acid, tridecanoic acid, myristic acid, tetradecanoic acid, pentadecanoic acid, palmitic acid, hexadecanoic acid, margaric acid, heptadecanoic acid, stearic acid, octadecanoic acid, arachidic acid, and icosanoic acid.

Dicarboxylic acids of the present invention are organic compounds that contain two carboxylic acid groups. Such dicarboxylic acids may comprise additional heteroatoms, such as oxygen, nitrogen, or sulfur. Dicarboxylic acids may be aliphatic or aromatic. Aside from the two —COOH groups, dicarboxylic acids may be saturated or unsaturated. The dicarboxylic acids may be represented by the formula HOOC—R—COOH, wherein R is a di-functional organic group, such as alkylene, alkenylene, alkynylene, arylene, and any of the preceding modified by a one or more heteroatoms.

Examples of dicarboxylic acids include compounds such as alkylene dicarboxylic acids, having the general formula HOOC—$(CH_2)_n$—COOH wherein n is 0 to 12; mono-unsaturated forms thereof; di-unsaturated forms thereof; tri-unsaturated forms thereof; and polyunsaturated forms thereof. Specific examples of dicarboxylic acids include oxalic acid, ethanedioic acid, malonic acid, propanedioic acid, succinic acid, butanedioic acid, glutaric acid, pentanedioic acid, adipic acid, hexanedioic acid, pimelic acid, heptanedioic acid, suberic acid, octanedioic acid, azelaic acid, nonanedioic acid, sebacic acid, decanedioic acid, undecanedioic acid, and dodecanedioic acid. Examples of aromatic dicarboxylic acids include phthalic acid, benzene-1,2-dicarboxylic acid, o-phthalic acid, isophthalic acid, benzene-1,3-dicarboxylic acid, m-phthalic acid, terephthalic acid, benzene-1,4-dicarboxylic acid, and p-phthalic acid.

Examples of monounsaturated acids include maleic acid, (Z)-butenedioic acid, fumaric acid, (E)-butenedioic acid, glutaconic acid, pent-2-enedioic acid, traumatic acid, and dodec-2-enedioic acid. Examples of di-unsaturated acids includes three isomeric forms of muconic acid, and (2E,4E)-hexa-2,4-dienedioic acid.

In some embodiments, the product of the reaction step 100 may optionally be subjected to other chemical and/or physical separation technologies. For example, some high-valued minerals and chemicals may be retrieved from the reaction product using conventional chemical and/or physical separation methods. Such chemicals include, for example, oxo-chemicals. Applicable chemical and physical separation technologies that may be used include any of those known to one skilled in the art, including fractional distillation, liquid/liquid extraction, adsorption, chromatography, ion exchange, membrane filtering, and hybrid systems.

In FIG. 1, the product of reaction step 100, with or without extraction of the minerals and high-value chemicals, may be subjected to microbial digestion 400. These products may be introduced to a microbial digester, where the solubilized carbonaceous materials undergo a bioconversion process. During the bioconversion process, some or all of the solubilized carbonaceous materials are digested by microorganisms in the microbial digester. In one embodiment, the bioconversion process may produce biogases such as methane, hydrogen, carbon monoxide, other gases and mixtures thereof, which may be used as fuel or can be converted to electricity.

The conditions in the microbial digester may be optimized to achieve the greatest degree biodegradation of the solubilized carbonaceous materials in the digester. Conditions that may be optimized include one or both of the degree and rate of bioconversion. The products of reaction step 100 may affect one or both of the degree and rate of bioconversion in this subsequent bioconversion step. Thus, in one aspect of the invention, the conditions of the reaction step 100 are selected on the basis of yielding products that have a larger quantity of biodegradable materials and/or to provide an enhanced rate of biodegradation.

The microbial digester may be either an aerobic digester or an anaerobic digester, or a combination of the two. In some embodiments, both aerobic and anaerobic digesters may be used. Aerobic digestion and anaerobic digestion typically provide different products. Thus, aerobic and anaerobic digestion may function complimentarily. In some embodiments, the microbial digester may be a partial anaerobic digester, which may be configured such that only portion of the microbial digester is exposed to oxygen. At another portion of the microbial digester, the oxygen has been essentially consumed and thus this portion of the microbial digester functions as an anaerobic digester. In this partial anaerobic digester, the solubilized carbonaceous materials pass from the aerobic portion to anaerobic portion of the microbial digester such that the solubilized carbonaceous materials are subjected to both aerobic digestion and anaerobic digestion. In some embodiments, the microbial digester may be supplied with limited oxygen. After the initial aerobic digestion, the oxygen is essentially consumed. Then the digester becomes an anaerobic digester.

The microbial digester may contain microbes in the form of a single species or strain of a microorganism, multiple species or strains of microorganisms or a microorganism consortium. These microorganisms are used to digest the solubilized carbonaceous materials, such as low molecular weight organic compounds, to other products of interest, including gases such as methane and hydrogen, liquids such as organic acids and alcohols, and solids such as oxo-aromatics. For example, two or more different reactions may be carried out in a single microbial digester by introduction of different microorganisms. Concentrations of microorganisms may also be varied to alter the relative reaction rates thereby influencing the digestion product mixture, particular in situations where microorganisms compete for the same substrates. A particular microorganism that is involved in a rate-limiting step of the bioconversion process may be supplemented to increase the reaction rate or yield of that rate-limiting step.

In embodiments employing a microorganism consortium, different species of microorganisms may be provided for different purposes. For example, a particular microorganism can be introduced for the purpose of increasing a nutrient, decreasing a concentration of a toxin, and/or inhibiting a competing microorganism for another microorganism in the consortium that participates in the conversion process. One or more species of microorganisms may be introduced to accomplish two or more of these purposes.

The microorganisms may be naturally occurring or may be synthesized from naturally occurring strains. Furthermore, the microorganisms may incorporate genetically modified organisms. These microorganisms may include fungi, bacteria, archaea, and combinations thereof. The microorganisms are typically selected based on metabolic pathways that achieve conversion of carbonaceous molecules to specific products of interest.

In some embodiments, at least one nutrient may be introduced to the microbial digester. The nutrients may be substances upon which one or more species of microorganism is dependent or the nutrients may be substances that can or will be converted to a substance upon which one or more species of microorganism is dependent. Suitable nutrients for the present invention include ammonium, ascorbic acid, biotin, calcium, calcium pantothenate, chlorine, cobalt, copper, folic acid, iron, $K_2HPO_4$, $KNO_3$, magnesium, manganese, molybdenum, $Na_2HPO_4$, $NaNO_3$, $NH_4Cl$, $NH_4NO_3$, nickel, nicotinic acid, p-aminobenzoic acid, biotin, lipoic acid, mercaptoethanesulfonic acid, nicotinic acid, phosphorus, potassium, pyridoxine HCl, riboflavin, selenium, sodium, thiamine, thioctic acid, tungsten, vitamin B6, vitamin B2, vitamin B1, vitamin B12, vitamin K, yeast extract, zinc and mixtures of one or more of these nutrients.

In some embodiments, at least one enzyme may also be added to the microbial digester. The enzymes can be used, for example, to enhance the conversion of the solubilized carbonaceous materials. For example, an enzyme may be used to assist a specific conversion reaction, preferably a rate limiting reaction, in the bioconversion process. In some exemplary embodiments, enzymes may be used to further to enhance the yield, rate and/or selectivity of the bioconversion process, or a substance that inhibits growth of at least one species inhibitory to the yield, rate and/or selectivity of the conversion process.

The enzymes that are suitable for the present invention may include Acetyl xylan esterase, Alcohol oxidases, Allophanate hydrolase, Alpha amylase, Alpha mannosidase, Alpha-L-arabinofuranosidase, Alpha-L-rhamnosidases, Ammoniamonooxygenase, Amylases, Amylo-alpha-1,6-lucosidase, Arylesterase, Bacterial alpha-L-rhamnosidase, Bacterial pullanases, Beta-galactosidase, Beta-glucosidase, Carboxylases, Carboxylesterase, Carboxymuconolactone decarboxylase, Catalases, Catechol dioxygenase, Cellulases, Chitobiase/beta-hexo-aminidase, CO dehydrogenase, CoA ligase, Dexarboxylases, Dienelactone hydrolase, Dioxygenases, Dismutases, Dopa 4,5-dioxygenase, Esterases, Family 4 glycosylhydrolases, Glucanaeses, Glucodextranases, Glucosidases, Glutathione S-transferase, Glycosyl hydrolases, Hyaluronidases, Hydratases/decarboxylases, Hydrogenases, Hydrolases, Isoamylases, Laccases, Levansucrases/Invertases, Mandelate racemases, Mannosyl oligosaccharide glucosidases, Melibiases, Methanomicrobialesopterin S-methyltransferases, Methenyl tetrahydromethanopterin cyclohydrolases, Methyl-coenzyme M reductase, Methylmuconolactone methyl-isomerase, Monooxygenases, Muconolactone delta-isomerase, Nitrogenases, O-methyltransferases, Oxidases, Oxidoreductases, Oxygenases, Pectinesterases, Periplasmic pectate lyase, Peroxidases, Phenol hydroxylase, Phenol oxidases, Phenolic acid decarboxylase, Phytanoyl-CoA dioxygenase, Polysaccharide deacetylase, Pullanases, Reductases, Tetrahydromethan-opterin S-methyltransferase, Thermotoga glucanotransferase and Tryptophan 2,3-dioxygenase.

In some embodiments, carbon dioxide, carbon monoxide, and hydrogen produced in the reaction step 100 may also be fed to the microbial digester, where specific microorganisms can convert these gases to small organic acids, alcohols, methane, and combinations thereof.

The following examples are illustrative, but not limiting, of the methods of the present disclosure. Other suitable modifications and adaptations of the variety of conditions and parameters normally encountered in the field, and which are obvious to those skilled in the art, are within the scope of the disclosure.

Figure 3:
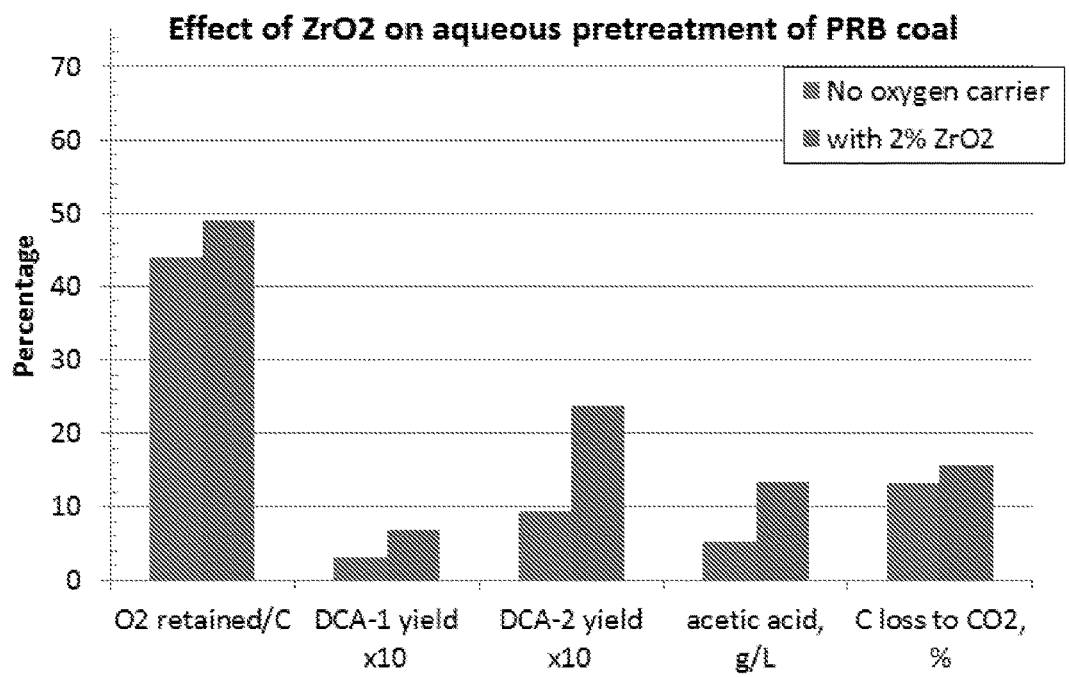
FIG. 3 is a plot showing increases in the amounts of some soluble products that result from a process using metal oxide oxygen carriers as described in Example 1.

EXAMPLE 500 g of a Powder River Basin (PRB) coal slurry was placed in a 2-L vessel and was the pressurized to 888 psi with air and then heated to 217° C. and was held at the temperature for 8 minutes. In a similar vessel, this process was repeated with 0.4 g of $ZrO_2$ (2% $ZrO_2$/coal ratio) added to the vessel. The gaseous and liquid products from these two vessels were separately analyzed. The results in terms of yields of acetic acid and two dicarboxylic acids (DCA) on a feedstock basis, as well as carbon loss to $CO_2$ and oxygen incorporation in the liquid products, are shown FIG. 3. The product included a variety of small organic molecules such as succinic acid (2.49%), malic acid (0.59%), fumaric acid (0.36%), glutaric acid (0.19%), propane 1,2,3-tricarboxylic acid (0.15%), and heptanoic acid (0.10%). See FIG. 3 for a GCMS spectrum of the acid fraction of this exemplary reaction of the present invention.

With $ZrO_2$ added to the vessel, the acid yields are significantly higher as compared with the process where no $ZrO_2$ was added. Oxygen incorporation as measured by oxygen consumed (but not lost to $CO_2$) also improved in the presence of $ZrO_2$, while there was also a slight increase in carbon loss to $CO_2$.

Other embodiments of the present disclosure will be apparent to those skilled in the art from consideration of the specification and practice of the embodiments disclosed herein. It is intended that the specification and examples be considered as exemplary only, with a true scope of the disclosure being indicated by the following claims.

The foregoing embodiments are susceptible to considerable variation in practice. Accordingly, the embodiments are not intended to be limited to the specific exemplifications set forth herein. Rather, the foregoing embodiments are within the spirit and scope of the appended claims, including the equivalents thereof available as a matter of law.

All documents mentioned herein are hereby incorporated by reference in their entirety or alternatively to provide the disclosure for which they were specifically relied upon.

The applicant(s) do not intend to dedicate any disclosed embodiments to the public, and to the extent any disclosed modifications or alterations may not literally fall within the scope of the claims, they are considered to be part hereof under the doctrine of equivalents.

What is claimed is:

1. A method for solubilizing a carbonaceous feedstock, comprising the steps of:
   a. reacting a mixture of the carbonaceous feedstock with a solid metal oxide on an inert support including a metal at a first, higher oxidation state to reduce the metal of the metal oxide to a second, lower oxidation state by releasing at least one oxygen atom to oxidize at least one component of the carbonaceous feedstock and the weight ratio of the solid metal oxide to the carbonaceous feedstock is in a range of from about 0.1:100 to about 10:100 to solubilize the carbonaceous feedstock;
   b. digesting the solubilized carbonaceous feedstock with at least one microorganism;
   c. oxidizing at least a portion of the metal or metal oxide containing the metal at the second, lower oxidation state to the first, higher oxidation state, and
   d. recycling at least a portion of the metal oxide containing the metal at the first, higher oxidation state from step (c) back to step (a).

2. The method of claim 1, wherein the metal oxide comprises a transition metal selected from the group consisting of lanthanides and actinides.

3. The method of claim 1, where the metal oxide comprises a metal selected from Fe, Ti, Cu, Ni, V, Cr, Mn, Co, Mo, La, Ce, Zr, Sr, W, Rh, Ba, Pt, Pd, and Ag.

4. The method of claim 1, wherein the inert support comprises a material selected from carbon, activated carbon, pumice, alumina, silica, silica-alumina, magnesia, diatomaceous earth, bauxite, titania, zirconia, clay, magnesium silicate, silicon carbide, zeolites, ceramics, carborundum, quartz, thoria, chromite, rutile, illmenite zircon, bauxite and combinations thereof.

5. The method of claim 1, further comprising the step of heating the inert support prior to step (a) to enable transfer of heat from the insert support to the mixture in step (a).

6. The method of claim 1, wherein the inert support is in a form selected from particles, extrudates, monoliths, fibers, mesh, and a net.

7. The method of claim 1, wherein step (a) is conducted in the presence of at least one oxidizing agent.

8. The method of claim 7, wherein the at least one oxidizing agent is selected from the group consisting of air, oxygen-enriched air, oxygen, ozone, perchlorates, carbon dioxide, nitrous oxide, oxides, superoxides, permanganates, chlorates, peroxides, hypochlorites and nitrates.

9. The method of claim 7, wherein the at least one oxidizing agent comprises a cation selected from metal, hydrogen and ammonium ions.

10. The method of claim 1, wherein step (a) is performed at a temperature in a range of from about 140° C. to about 270° C.

11. The method of claim 1, wherein step (a) is performed at a pressure in a range of from about 200 psia to about 1000 psia.

12. The method of claim 1, wherein the mixture reacted in step (a) comprises at least one solubilizing agent selected from the group consisting of mineral acids and mineral bases.

13. The method of claim 1, wherein step (a) is configured as multiple sequential steps.

14. The method of claim 13, wherein each of the multiple sequential steps is carried out with at least one difference in a reaction condition of temperature, pressure and duration, or a composition of an oxidizing agent.

15. The method of claim 1, wherein step (a) is performed for a duration of from about 1 minute to about 5 hours.

16. The method of claim 1, wherein the digesting step is a process selected from an aerobic process, an anaerobic process and a combination of an aerobic process and an anaerobic process.

17. The method of claim 1, wherein the carbonaceous feedstock is selected from the group consisting of coal, lignite, tar sands, tars, crude oils, peat, pitch, resins, lignin, latex rubber, waxes, agricultural wastes, bark, wood, and algae cake.

18. The method of claim 1, wherein step (a) is performed in a reaction vessel selected from a bubble column reactor and a trickle bed reactor.

* * * * *